(12) United States Patent
Budd

(10) Patent No.: US 7,394,530 B2
(45) Date of Patent: Jul. 1, 2008

(54) SURFACE INSPECTION TECHNOLOGY FOR THE DETECTION OF POROSITY AND SURFACE IMPERFECTIONS ON MACHINED METAL SURFACES

(76) Inventor: Gerald W. Budd, 36853 Healferton Rd., Farmington, MI (US) 48335

( * ) Notice: Subject to any disclaimer, the term of this patent is extended or adjusted under 35 U.S.C. 154(b) by 334 days.

(21) Appl. No.: 11/095,960

(22) Filed: Mar. 30, 2005

(65) Prior Publication Data

US 2005/0220335 A1   Oct. 6, 2005

Related U.S. Application Data

(60) Provisional application No. 60/557,490, filed on Mar. 30, 2004.

(51) Int. Cl.
*G01N 21/00* (2006.01)
(52) U.S. Cl. ................... 356/237.1; 356/237.2
(58) Field of Classification Search ............. 356/237.2; 148/420, 437, 237.2, 120; 164/46, 97, 113–114, 164/120–122, 487, 45, 420–437; 324/303; 429/13, 30, 40–44
See application file for complete search history.

(56) References Cited

U.S. PATENT DOCUMENTS 3,766,387 A * 10/1973 Heffan et al. ................. 378/58

| | | | |
|---|---|---|---|
| 4,582,993 A * | 4/1986 | Bhattacharya et al. | ... 250/359.1 |
| 4,803,639 A * | 2/1989 | Steele et al. | ................... 702/40 |
| 4,819,256 A * | 4/1989 | Annis et al. | .................... 378/87 |
| 5,715,334 A * | 2/1998 | Peters | ......................... 382/254 |
| 6,693,708 B1 * | 2/2004 | Hunter | ..................... 356/237.5 |
| 6,718,053 B1 * | 4/2004 | Ellis et al. | ..................... 382/128 |
| 7,148,960 B2 * | 12/2006 | Schuster et al. | .......... 356/237.6 |

* cited by examiner

*Primary Examiner*—Layla G. Lauchman
*Assistant Examiner*—Jarreas Underwood

(57) ABSTRACT

The present invention describes a method and apparatus for the detection and measurement of surface imperfections within a predetermined size range, contained on the surface of a machined cast metal component. The invention provides a novel illumination and image acquisition technique that allows the inspection of large cast machined surfaces without movement of the component, sensor or illumination system during acquisition of an image. The invention allows for the inspection of large surfaces on objects up to 1,000 mm×650 mm in size. The inspection field of view can be divided in multiple regions, defined by computer aided design (CAD) model data. Each of these regions may apply a unique set of inspection criteria used for disposition of the component. Inspection regions generated using CAD drawings indicate exact position of features with respect to the manufacturing datum located on the surface and viewable as part of the acquired image.

20 Claims, 10 Drawing Sheets

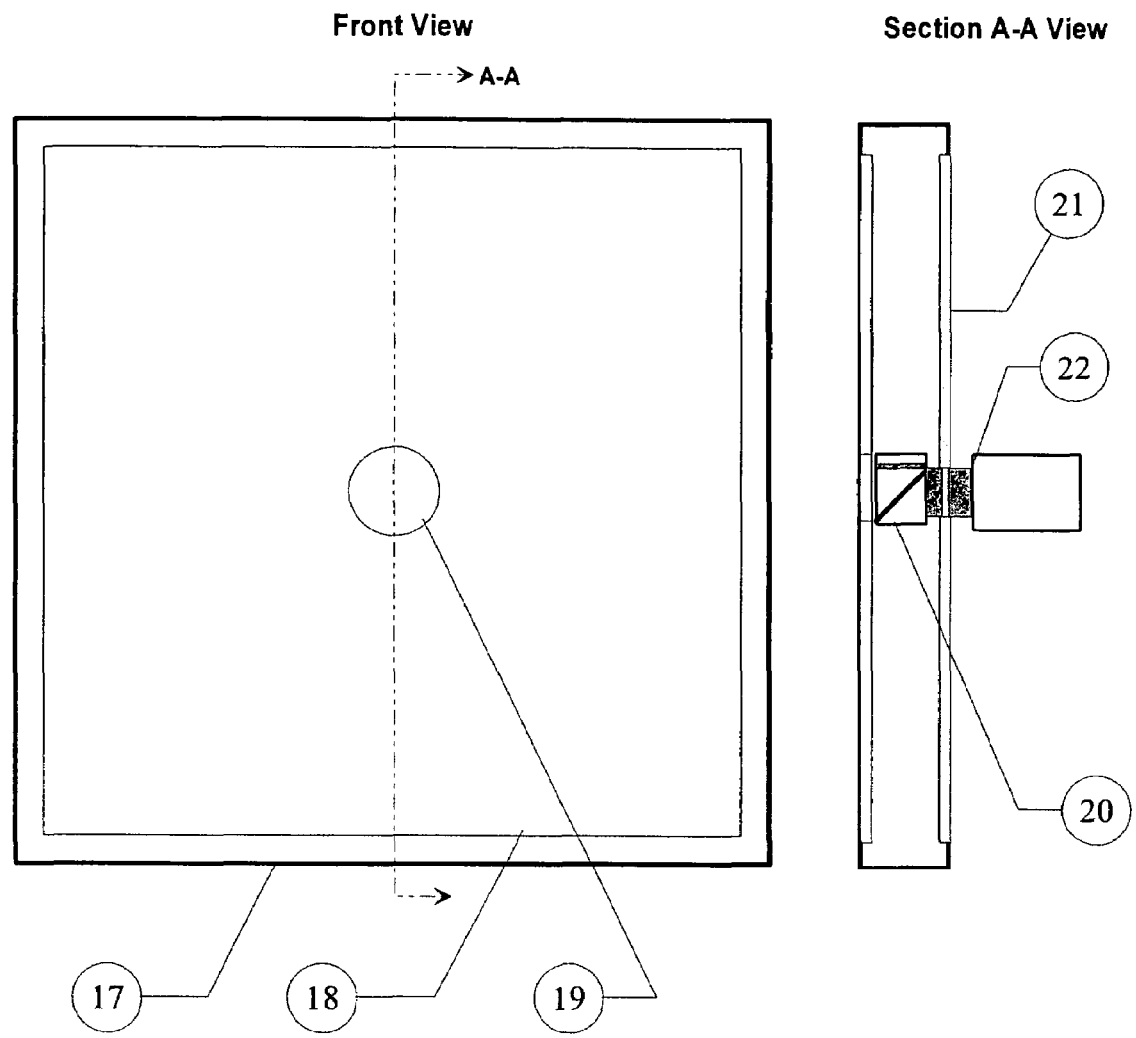

FIG. 3
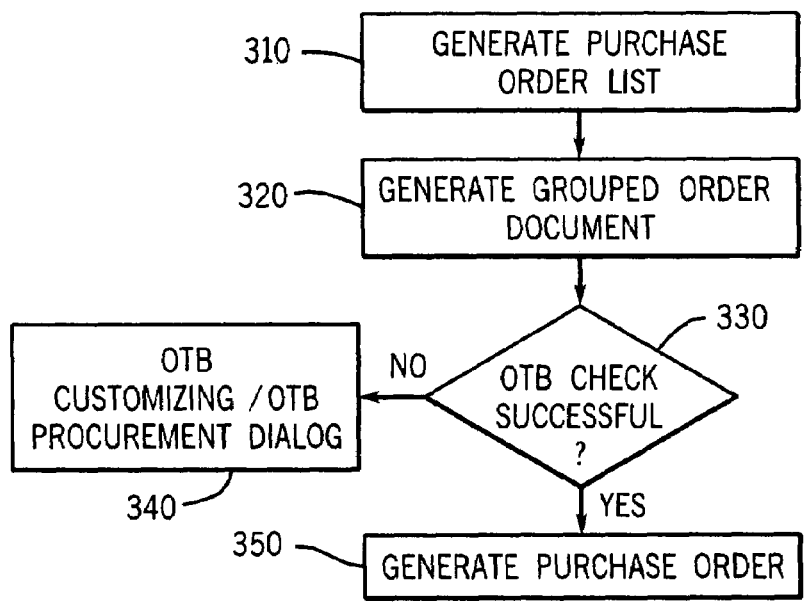
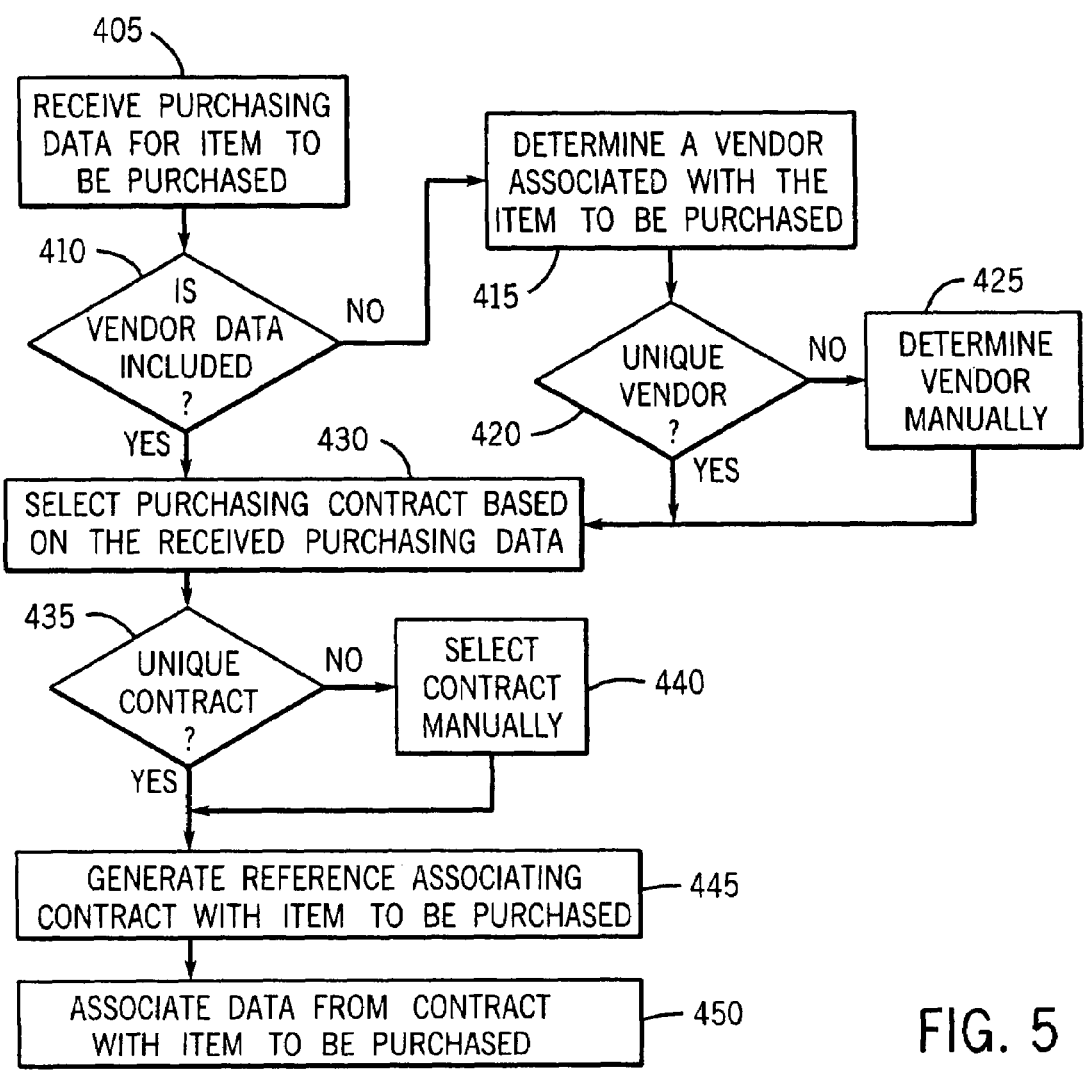
FIG. 5

FIG. 4

| Box | No. | Item | Origin | Article (Variant, lot) | Latest PO date | Vendor | Deliverz Date GR Ramp | Price | Quantity | UoM | Site |
|---|---|---|---|---|---|---|---|---|---|---|---|
| - | 12345678 | 10 | EKL | 471100 | 13/09/2002 | 100006 | 01/03/2003 | 1000 | 100 | CAR | VZ01 |
| - | 12345678 | 20 | EKL | 471200 | 20/09/2002 | 200003 | 15/03/2003 | 500 | 10 | CAR | VZ01 |
| - | 12345678 | 30 | EKL | 4713001 | 23/09/2002 | 100006 | 20/03/2003 | 69 | 1 | PC | VZ01 |
| - | 12345678 | 40 | EKL | 4713002 | 23/09/2002 | 100006 | 20/03/2003 | 69 | 1 | PC | VZ01 |
| - | 12345678 | 50 | EKL | 4713003 | 23/09/2002 | 100006 | 20/03/2003 | 89 | 1 | PC | VZ01 |
| - | 98765432 | 10 | EKL | 4714001 | 23/09/2002 | 200004 | 20/03/2003 | 89 | 1 | PC | VZ01 |
| - | 98765432 | 20 | EKL | 4714002 | 25/09/2002 | 200004 | 30/09/2003 | 89 | 1 | PC | VZ01 |
| - | 98765432 | 30 | EKL | 4714003 | 25/09/2002 | 200004 | 30/09/2003 | 89 | 1 | PC | VZ01 |
| - | 98765432 | 40 | EKL | 4714004 | 25/09/2002 | 200004 | 30/09/2003 | 89 | 1 | PC | VZ01 |
| - | 98765432 | 50 | EKL | 4714005 | 23/09/2002 | 100006 | 25/06/2003 | 10 | 25 | CAR | VZ01 |
| - | $0000001 | 10 | ADH | 471500 | 23/09/2002 | 100006 | 23/04/2003 | 20 | 80 | CAR | VZ01 |
| - | $0000002 | 10 | ADH | 471600 | 20/10/2002 | 100006 | 23/04/2003 | 30 | 20 | PC | VZ01 |
| - | $0000002 | 20 | ADH | 480000 | 20/10/2002 | 100006 | 23/04/2003 | 10 | 120 | CAR | VZ01 |
| - | $0000003 | 10 | ADH | 491200 | | | | | | | |

| Box | Article (Variant, Lot) | Latest Purchase Order Date | Vendor | Delivery Date GR Ramp | Price | Quantity | UoM | Site |
|---|---|---|---|---|---|---|---|---|
| | 471500 | 23/09/2002 | 100006 | 25/06/2003 | 10 | 25 | KAR | VZ01 |

822 →

| Box | Article (Variant, Lot) | Latest Purchase Order Date | Vendor | Delivery Date GR Ramp | Price | Quantity | UoM | Site |
|---|---|---|---|---|---|---|---|---|
| | 471600 | 9/23/2002 | 100006 | 4/23/2003 | 20 | 80 | KAR | VZ01 |
| | 480000 | 10/20/2002 | 100006 | 4/23/2003 | 30 | 20 | ST | VZ01 |

800 →

| Box | No. | Item | Origin | Article (variant, lot) | Latest PO Date | Vendor | Delivery Date GR Ramp | Price | Quantity | UoM | Site | | | Status |
|---|---|---|---|---|---|---|---|---|---|---|---|---|---|---|
| | $0000001 | 10 | ADH | 471500 | 9/23/2002 | 100006 | 6/25/2003 | 10 | 25 | KAR | VZ01 | | | |
| | $0000002 | 10 | ADH | 471600 | 9/23/2002 | 100006 | 4/23/2003 | 20 | 80 | KAR | VZ01 | | | |
| | $0000002 | 20 | ADH | 480000 | 10/20/2002 | 100006 | 4/23/2003 | 30 | 20 | ST | VZ01 | | | |

FIG. 10

| ORDER LIST (CHANGE) | | | | | | | | | | | |
|---|---|---|---|---|---|---|---|---|---|---|---|
| PURCH.ORG.\PURCH. GRP\VENDOR\BESTELLTYP\OR... | E. | H. | V. | N. | M. | O. | Fr... | F | D. | | |
| ▽ 20040716 | | | | | | | △ | | ⊗ | | |
| 4300006904 | | | | | | | △ | | ⊗ | | |
| 4300006965 | | | | | | | △ | | ⊗ | | |
| ▽ 20040717 | | | | | | | △ | | ⊗ | | |
| 4300006968 | | | | | | | △ | | ⊗ | | |
| ▽ 20040719 | | | | | | | △ | | ⊗ | | |
| 4300006875 | | | | | | | △ | | ⊗ | | |
| 4300006877 | | | | | | | △ | | ⊗ | | |
| 4300006878 | | | | | | | △ | | ⊗ | | |
| ▽ 20040720 | | | | | | | △ | | ⊗ | | |
| 4300001461 | | | | | | | △ | | ⊗ | | |
| 4300001476 | | | | | | | △ | | ⊗ | | |
| ▽ 20040723 | | | | | | | △ | | ⊗ | | |
| 4300006948 | | | | | | | △ | | ⚙ | | |
| ▽ 20040725 | | | | | | | △ | | ⊗ | | |
| 4300005828 | | | | | | | △ | | ⊗ | | |
| 4300005829 | | | | | | | △ | | ⊗ | | |
| 4300005830 | | | | | | | △ | | ⊗ | | |

FAST DATA ENTRY

| OTYP | PORG | PGR | PLANT | VENDOR | DELIVERY DATE | MATE |
|---|---|---|---|---|---|---|
| NB | | | | LIF_MLA | | |

ORDER LIST ENTRIES

| SEL... | POSNR | TYPE | PORG | PGS | VENDOR | LIF_MLA | MATE | MLA |
|---|---|---|---|---|---|---|---|---|
| ⇨ | 4300006948 | NB | ESLI | 001 | | | | |
| | $ 15 | | | | | | | |
| | $ 16 | | | | | | | |
| | $ 17 | | | | | | | |
| | $ 18 | | | | | | | |
| | $ 19 | | | | | | | |

| Box | No. | Item | Ordin | Article (Variant, Lot=) | Latest PO Date | Vendor | Delivery Date GR Ramp | Price | Currency | Quantity | UoM | Site | Order No. | PO Item | Status |
|---|---|---|---|---|---|---|---|---|---|---|---|---|---|---|---|
| ( | 12345678 | 10 | EKL | 471100 | 13/09/2002 | 100006 | 01/03/2003 | 1000 | EUR | 100 | CAR | VZ01 | 4500000000 | 00010 | ◐◯ |
| ( | 12345678 | 20 | EKL | 471200 | 20/09/2002 | 200003 | 15/03/2003 | 500 | EUR | 10 | CAR | VZ01 | 4500000001 | 00010 | ◐◯ |
| ( | 12345678 | 30 | EKL | 4713001 | 23/09/2002 | 100006 | 20/03/2003 | 69 | EUR | 1 | PC | VZ01 | 4500000002 | 00010 | ◐◯ |
| ( | 12345678 | 40 | EKL | 4713002 | 23/09/2002 | 100006 | 20/03/2003 | 69 | EUR | 1 | PC | VZ01 | 4500000002 | 00020 | ◐◯ |
| ( | 12345678 | 50 | EKL | 4713003 | 23/09/2002 | 200004 | 20/03/2003 | 69 | EUR | 1 | PC | VZ01 | 4500000002 | 00030 | ◐◯ |
| ( | 98765432 | 10 | EKL | 4714001 | 23/09/2002 | 200004 | 20/03/2003 | 89 | EUR | 1 | PC | VZ01 | 4500000003 | 00010 | ◐◯ |
| ( | $0000001 | 10 | ADH | 471500 | 23/09/2002 | 100006 | 25/06/2003 | 10 | EUR | 25 | CAR | VZ01 | 4500000004 | 00010 | ◐◯ |
| ( | $0000002 | 10 | ADH | 471600 | 23/09/2002 | 100006 | 23/04/2003 | 20 | EUR | 80 | CAR | VZ01 | 4500000005 | 00010 | ◐◯ |

FIG. 11

SURFACE INSPECTION TECHNOLOGY FOR THE DETECTION OF POROSITY AND SURFACE IMPERFECTIONS ON MACHINED METAL SURFACES

CROSS-REFERENCE TO RELATED APPLICATIONS

I claim priority to my Provisional Patent Application No. 60/557,490 with filing date Mar. 30, 2004.

FIELD OF THE INVENTION

This invention relates to the procedures and devices utilized in the optical inspection of metal and non-metal components for the presence of surface imperfection and particularly to inspection of porosity on machined aluminum castings.

BACKGROUND OF THE INVENTION

The author of this invention has worked in the field of machine vision inspection for over 15 years. There have been many advancements in the field of machine vision during the past ten years, in particular the speed at which the image processing algorithms can process the information. There have also been advances in the resolution of the sensor (CCD and CMOS) used to acquire the images of objects under inspection. Industry, in particular the aerospace and automotive industries have long desired a robust method for the detection of surface porosity. Small pores or holes that appear on the surface of a machined metal component divulge the evidence of porosity.

There are three types of porosity produced from different root causes. The term "Gas Porosity" refers to hydrogen gas within a casting. Molten aluminum has such an affinity for hydrogen that it will disassociate it from other molecules, such as water and form a solution with it. As with most solutions, as the temperature drops the hydrogen becomes less soluble and precipitates as hydrogen gas. The greater the amount of hydrogen in the molten aluminum and the slower it solidifies the greater the hydrogen voids will be. These voids are generally smooth, round or slightly elongated and may be somewhat localized to the areas of the casting that solidify last. This type of porosity is generally undetectable visually since the surface of the casting solidifies quickest preventing the hydrogen from forming holes large enough to be visible on the surface except by using fluorescent penetrant inspection. However, after the removal of material from the surface of the casting by a machining operation the porosity generally becomes visible.

The term "Gas Holes" refers to generally large and more localized voids than gas porosity but they retain the smooth, round or slightly elongated shape. They are usually caused by reaction in the mold media producing gas that will bubble through the molten metal. This type of porosity is generally appears as larger voids on the surface of castings after machining operations.

The term "Shrinkage Porosity" refers to a type of porosity that has a rough irregular shape. It is caused by a lack of adequate feed metal during solidification. This type of porosity is extreme and is observed as variations in the casting shape or voids in the surface.

The detection methods used for porosity depend on the type of porosity. If the only concern is porosity exposed on the surface of a casting then limits can be set for the maximum allowable size. Visual inspection standards are assigned and human inspection is the preferred technique. However, if internal porosity is the major concern, then radiography (x-ray inspection) is the most common detection method. There are other inspection technologies that can be used for the detection of internal flaws they include Eddy Current Inspection, Fluorescent (Dye) Penetrant Inspection, and scanning electron microscopy (SEM) Imaging. All of before mentioned techniques are usually applied in an area removed from the production environment, these are referred to as Off-Line inspection techniques.

The majority of "In-Process" or "On-Line" inspections for porosity related defects are normally performed by qualified human inspectors. The inspection tasks can be very difficult because of complex inspection specifications written to handle the wide variation of porosity characteristics. The size of the porosity is the primary characteristic. Any occurrence of porosity larger than a specified diameter (or dimension) constitutes a defective condition. The occurrence of two or more smaller defects within a specified proximity to each other also constitutes a defective condition. If more than a specified number of porosity defects appear on the entire component this constitutes as defective condition. If the density of smaller dimension porosity that are not considered a defective condition individually but are present as a cluster (small proximity as specified in the specification) then this condition will constitute a defective condition. The number of conditions constituting a defective condition can be considered an overwhelming task of the human inspector and often results in acceptable product being rejected as "bad" or defective product being accepted as "good".

The specification of porosity limits for commercial castings may use MIL-STD-2175, ASTM B26, Aluminum Association's AA-CS-M Series, ASTM E155 (Radiometric) or the inspection or engineering specifications of the individual customer. Most engineering porosity inspection specifications have been written for human inspection. There is currently a realization by engineering and inspection departments that the specifications must be revised to take advantage of the developing automated machine vision inspection technology described in this present invention.

The configuration and position of the essential components with respect to each other is very important to the functionality of the present invention. The location of the illumination system with respect to the image sensor is critical, and will determine the type and size of imperfections that can be detected. The resolution of the image sensor is an important factor in ability of the invention to reliably isolated imperfections (such as porosity) from background information. The capability of the present invention improves with the use of larger the image sensors and the number of picture elements (Pixels) implemented in the sensors. The current technology implements image sensors that range in size from 640 (Horizontal)×480 (Vertical) to 4000 (Horizontal)×4000 (Vertical) pixels. The resolving capability of the invention will improve as a function of increasing the number of available pixels in the acquisition device. When viewing objects that are rectangular in shape the present invention implements a sensor with format that closely mirrors the shape of the object, such as a sensor with a pixel resolution of 3,500 (H)×2,600 (V).

The defect detection can be estimated using the simple formula $$\text{Feature Resolution (mm/pixel)} = \frac{(FOV \text{ in mm})}{\text{Sensor Resolution (\# pixels)}}$$

$$= \text{Length Dimension/pixel.}$$

Where smaller Feature Resolution values provide better detection of imperfections.

The typical implementation technique requires that imperfections must be larger than a single pixel. Image noise and background variations often generate information that is a single pixel in size and should be eliminated with filtering techniques used in the image processing system. A typical inspection can isolate imperfections with a diameter of 400 μm in a 500 mm FOV when using an 8-megapixel sensor. Higher resolution sensors can isolate even smaller imperfections. Another important factor in proper selection of sensor technology is the grayscale resolution, or depth of the image. The depth of the image is referenced in the number bits, the greater the number of bits the greater the signal to noise ratio of the image. A sensor with 8-bit grayscale resolution is capable of discerning 256 levels of gray information, $2^8=256$. An image sensor with 14-bit grayscale resolution is capable of identifying 16,384 unique levels of grayscale information. This is extremely important if you consider that the lowest two or three bits of the information as being subject to noise. In an 8-bit image, the lowest three bits correlates into 3.125% of the sensor's range. The lowest three bits of a 14-bit image is approximately 0.049% of the sensor's range. As future improvements of image sensor technology materialize the spatial resolution capabilities of the present invention will also improve.

The present invention provides a method and device that can perform the visual inspection of machined metal components for surface porosity defectives. The invention offers the unique capability of isolating surface porosity on all surfaces that are visible to an electronic imaging system and accurately measuring the size (dimensions) of the porosity defects. The individual measurements can then be applied to the one or more inspection criteria as set forth in an inspection specification. Furthermore, the present invention provides 100% inspection capability so that it can be applied on-line in the production environment maintaining a specified quality level of out-going product.

BRIEF SUMMARY OF THE INVENTION

It is an object of the present invention to transform the present probabilistic detection of surface imperfections, namely porosity with an area equivalent to or larger than 0.400 μm diameter, into a deterministic detection and accurate measurement process.

It is a further object of the present invention to provide a method to define the mechanical requirements to produce the capability of positioning the component(s) to be inspected in the defined inspection location.

It is a further object of the present invention to provide a method to position the acquired image(s) so as to coincide with one or more inspection masks, referred to hereafter as inspection zones. Each of the inspection zones can be assigned a unique or specific set inspection of criteria.

It is a further object of the present invention to provide a method to define the number, size and relative position of imperfections isolated within each of the defined inspection zones.

It is a further object of the present invention to provide a method to uniformly illuminate substantially the entire surface of the component to be inspected.

It is a further object of the present invention to provide a method to control the intensity of the illumination source so provide accurate and repeatable measurements over an extended period of time (6-18 months between lamp replacements) in the production environment.

It is a further object of the present invention to provide a method and device for the traceability of the components and the individual inspection results in a database.

It is a further object of the present invention to provide a method for the generation of point cloud measurements for defects to aid in the identification of areas where the porosity levels have a higher level of incidence.

It is another object of the present invention to provide a method for the identification of casting variations and detection of missing machined features.

The present invention provides an improved method for the detection and measurement of porosity, within a predetermined size range located on an exposed surface that can be viewed with the equipment described herein. The present invention provides for the interconnectivity of more than one sub-system when an application requires more than one sensor or more than one image processing computer. In such cases, one of the image processors may be used as the "Cell Controller" for all of the devices in the inspection system. The cell controller is responsible of compilation of all inspection results and it acts as the repository of the inspection system database. If the number of image processing units exceeds three units or if the workload of image processing/housekeeping exceeds the allocated cycle time of the inspection station, then a separate computer may be implemented as the cell controller.

A short description of the mechanical, electrical, optical and software procedures used for setup and operations of the present invention are provided here.

The training method comprises the steps of:
a) a "master" component, one that has been checked as meeting all the specifications necessary to qualify as a nominal part, is positioned in the image acquisition station of the invention;
b) an image of the master component is acquired using the same equipment and conditions that will be used for analysis of production components;
c) the location of the datum on the master are extracted from the image accurately using special software;
d) a set of inspection mask are created using the features of the master component and stored relative to the location of the datum;
e) a set of inspection algorithms are developed to extract and measure the relevant features located in each of the masks (zones) that correspond to the inspection criteria of each zone;

The method used by the present invention for the inspection of production components comprises the following steps:
f) the test component is precisely located inside the inspection chamber, positioned with the aid of locating pins, physical stops or recessed lock positions within the inspection fixture;
g) the invention acquires the necessary image or images;
h) the image or images are translated (and rotated if necessary) to coincide with the datum of the reference images;

i) a mask (inspection zone) and corresponding vision algorithm is applied to the acquired image and the result is then stored in the appropriate database register;

j) the inspection criteria is applied to results of each corresponding inspection zone and evaluated to determine if the test component pass or failed;

k) each components test either was previously marked with a unique identification or will be marked at the conclusion of the inspection for traceability;

l) the invention has the ability to record the every image and the location of any defective conditions in the image in the database;

m) the complete database and all associated images are stored on optical disk for future review;

n) the steps f) through m) are repeated for each component to be inspected of the same model (part number;

wherein said sensor being mounted inside a sealed enclosure the critical optical components of the system can be protected from the environment. The detector is mounted in such a manner so that so that the optical path can be easily adjusted with the target area. The design of the sensor enclosure allows for the insertion of optical filter elements within the optical path of the invention. The image processing computers and sensitive electronic components are housed in climate controlled electrical enclosures with power protection to insure proper environmental conditions. These and other objects, features and advantages of the present invention will become more evident from the following discussion and drawings.

The preferred production line embodiment of the invention would use lift and carry transfer, powered roller, or transfer pallet with locating pins to register placement of component in the inspection station.

BRIEF DESCRIPTION OF THE SEVERAL VIEWS OF THE DRAWINGS

FIG. 2 illustrates a Diffuse Front Lighting System configuration with on-axis beam splitter to fill the hole that the sensor views through;

FIG. 3 is an actual image acquired using invention and datum locations;

FIG. 4 illustrates the Outer Inspection Zone on image of test component;

FIG. 5 illustrates the Inner Inspection Zone on image of test component;

FIG. 6 illustrates the Worm Trail Inspection Zone on image of test component;

FIG. 9 illustrates the Point Cloud of Defects for a large number of samples on the Inner and Outer Inspection Zones;

DETAILED DESCRIPTION OF THE INVENTION

Figure 1:
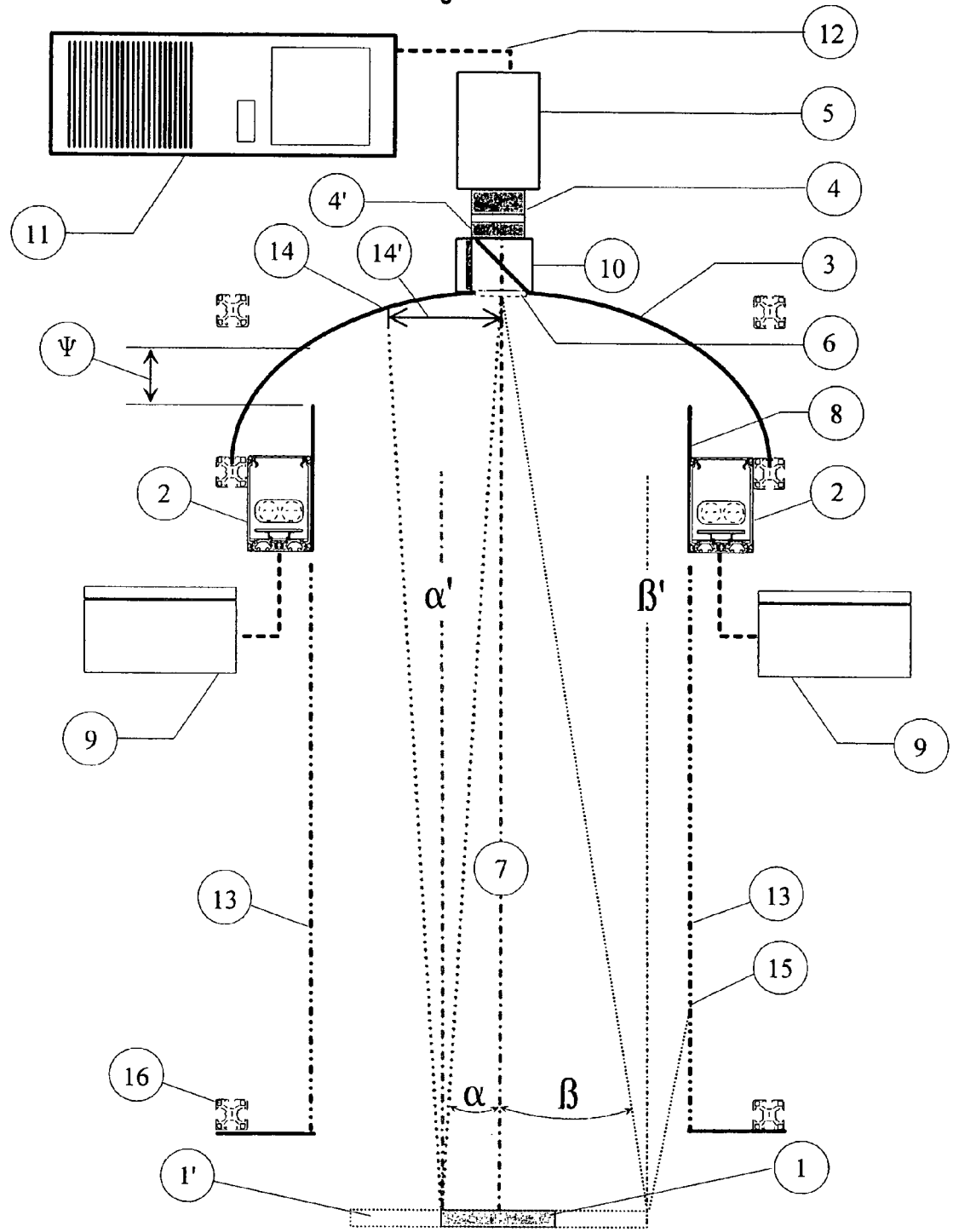
FIG. 1 illustrates the major components necessary to the invention to function and their relative position with respect to each other.

The present invention consists of several major components arranged in the proper configuration to produce image data that will yield repeatable measurements. The present invention, hereafter referred to as the "System" is comprised of several major components. The major components include 1) a mechanical device to aid in the location of the test components; 2) a high resolution image sensor (>3.2 megapixel); 3) a diffuse flat field illumination system with active-loop feedback control; 4) an image processor capable of supporting a minimum 65 MB of image memory; 5) specialized image processing software to extract surface imperfections; 6) special software to allow the communication of inspection parameters, data and results between devices; and 7) the necessary interface connections for the devices to exchange the data. The major components and their relationship to each other in the system are illustrated in FIG. 1. The system design allows it to inspect large surfaces using a single high-resolution sensor per surface. Typical applications of the present invention include the inspection of sealing surfaces of machined automotive, aerospace and heavy equipment components. The inspection of: the deck face of engine blocks; the lower pan mating surfaces of engine blocks; the mating surfaces of upper and lower intake engine manifolds; exhaust manifold mating surfaces; sealing surfaces of engine front covers; sealing surfaces of transmission components, machined cylinder bore surfaces, interior surface of fuel injector bores, the machined surfaces of accuator plates and any substantially flat machined surface are examples of typical use for the present invention.

The component that is to be inspected is hereafter referred to as the sample (item 1 or item 1' in FIG. 1). The present invention will inspect the sample for surface imperfections, the presence of cast and/or machined features and determine the relative position of certain features with respect to each other or a datum.

The lighting components implemented in the invention provide a uniform diffuse illumination field. The uniform illumination minimizes the amount of image processing necessary to isolate subtle imperfections and thus decreases the overall inspection cycle time. A unique tunnel lighting design allows the invention to illuminate large objects. The diffuse lighting system design can illuminate areas many times larger than any commercially available lighting product. The fluorescent lamps (item 2) are placed on at least two sides of the (matte reflecting tunnel structure) diffuse lighting tunnel structure (item 3) and driven with a high frequency power supply (item 9) implementing a closed-loop feedback circuit to maintain constant lamp output. The lamps do not illuminate the sample directly. The lamps are directed to illuminate the inside lower surface of the matte reflecting surface of the tunnel structure to create a uniform diffuse light source. The size of the tunnel structure is only limited by the physical constraints of the volume in which it must be implemented. The illumination is provided by a stable lighting system of sufficient size to provide adequate energy of image acquisition. The preferred embodiment of the lighting system will use high-output fluorescent lamps operating from an electronic ballast (item 9) driven at high frequency (>40 KHz, 55 KHz typical). The electronic ballast is connected to the lamps using the appropriate sized shielded umbilical cable. A photosensitive device, such as photo-diode or photo-detector must be used to monitor the luminous flux of the lamps and provide a closed loop feedback signal to electronic ballast to maintain the output at the desire level.

The illumination source must provide substantially uniform lighting across the surface to be inspected. A more consistent lighting field produced when the object is not directly illuminated by the light source (item 2). The diffuse illumination is provided by shinning the lamps on a (large diffuser) diffuse lighting tunnel structure (item 3) with a matte finish and allowing the scattered light to illuminate the object being inspected. The (diffuse reflector) diffuse lighting tunnel structure (item 3) generally will implement a parabolic or circular shape to help generate a uniform illumination field. The shape of the diffuse reflecting surface is adjusted to maximize the uniformity of the lighting. Small components with a narrow profile will implement a nearly semi-circle diffuser shape with its height equal to that of the radius. The shape of the diffuser is maintained by a super structure (item 16). The lighting system can be fluorescent, halogen, metal halide, light emitting diode (LED) or Electro-luminescent with a means to maintain a constant luminous flux output level.

An aperture (item 6) is placed in the diffuse reflector of the tunnel lighting that is large enough to allow the lens (item 4) of the image sensor (item 5) to view the sample without obstruction. In certain applications, it may be necessary to place an optical filter (item 4') between the sample and objective lens. The optical filter may be a polarizing filter, notch filter, or anti-reflective filter.

The alignment of components used for the illumination and image acquisition is very important. The center of the sample surface that is to be inspected is positioned to coincide with the axis of the sensor, this is referred to as the inspection axis (item 7). The distance from the image sensor to the sample is referred to as the "Working Distance" or WD and is determined primarily by the optical system and resolution requirements. The optical system is designed to minimize the optical distortion. The image sensor (item 5) is positioned so that the plane of the CCD or CMOS imaging device is made substantially parallel to the plane of the object to be inspected (item 1). By maintaining the parallel relationship between imaging plane and the plane of the inspected object, the errors caused by optical distortion and parallax will be minimized. A longer focal length lens reduces the effects of parallax but it also requires that the tunnel structure to be placed further away from the sample. The orientation of the inspection axis can be horizontal, vertical or any angle if the relative orientation of the components is maintained.

Described here is Method "A" for the creation of proper width tunnel illumination system. The angle created by the line of the inspection axis (item 7) and the extreme edge of the sample is the angular field of view and represented by angle ($\alpha$). The minimum width required for the illumination source can be calculated by placing a line placed at the edge of the sample drawn perpendicular to its surface ($\alpha'$) and then projecting a line at an angle ($\alpha$) away from the inspection axis. The distance from the inspection axis to the point at which this projected line intersects the diffuse tunnel surface (item 14) will define the ½ width of the illumination system represented by line 14'.

If the component is large and it is not feasible to construct a tunnel illumination source as wide as required by the design of method "A" an alternative Method "B" illumination system may be constructed. The width of the inspection system may be limited by physical space constraints by adjacent equipment. A larger sample is illustrated in FIG. 1 as item 1' and centered on the inspection axis (item 7). The minimum width for the illumination system may be reduced by inserting diffuse surfaces parallel to the inspection axis indicated in FIG. 1 by items 13. The angle $\beta$ is represented by the angle between the inspection axis (item 7) and a line that connects the center of the image sensor and the extreme edge of the sample. The minimum position of the lower edge of the vertical diffusing panels (items 13) can be calculated in the following manner. Place a line at the edge of the sample drawn perpendicular to its surface (line $\beta'$), then project a ray that emanates from that point at an angle ($\beta$) away from the inspection axis. This ray will intersect the vertical panel at point indicated by item 15. It is recommended that the panel extend longer than the intersection point to account for variation in sample placement.

To improve the sensitivity of the invention the sensor must be protected from having the illumination source enter the optical path directly. The present invention incorporates a small panel that attaches to the side of the illumination source to prevent the sensor/optical system from directly viewing the light source. This blocking panel (item 8) is constructed of either metal or plastic and is painted white to reflect the illumination energy toward the surface of tunnel structure. The gap (item X) created between the blocking panel (item 8) and the lower surface of the diffuse lighting tunnel structure (item 3) should be maximized to allow maximum amount of light into the inspection chamber.

The aperture (item 6) in the diffuse lighting tunnel structure (item 3) will not be seen on the surface of the sample if it small or the sample surface is also diffuse. However, under certain instances it may be desirable to hide the presence of the aperture. This can be achieved by placing a beam splitter with an LED lighting panel (item 10) on the perpendicular path between the sensor lens (item 4) and the sample (item 1). The amount of light emitting from the LED lighting panel is adjusted to match the intensity of the diffuse tunnel surface. The aperture will become imperceptible in the sample images acquired.

The image processing equipment (item 11) used in the present invention is an industrial computer. The rapid advancements in small central processing units (CPU's) transforms the system performance in to a moving target. In the present embodiment of the invention an Intel Pentium 4 CPU with a large internal cache running at a clock speed in excess of 3.2 GHz was implemented. The large image sensors produce very large images and require a minimum of 1 GB of memory to maximize system performance. The image processor incorporates Gigabyte (1000 MB) Ethernet for communication between devices. In the case of discrete device signals a rack of digital input and output modules provide optically isolated connection points that can be configured for AC or DC operation. Simple handshaking signals between devices are normally performed through the discrete I/O hardware. The image processor also incorporates one or more optical drives for recording inspection information and archival of acquired images used for sample traceability.

The majority of operations performed involve the transformation of the images the faster memory is implemented, present technology is DDR2 operating at 533 MHz. The acquisition of images is critical to the performance of the present invention and speed at which this information can be transferred from sensor to the image processor is equally important. The method of data transfer between sensor(s) and image processor(s) is via a special sensor cable (item 12). The preferred method of data transfer is one of the following GigaByte Ethernet, CameraLink, High Speed USB or Firewire. As with the advancements in the image processor the sensor transfer methods will improve and the present invention will implement the latest technology to insure performance enhancements.

The selection of the sensor size is determined by the minimum size of the surface imperfection or feature dimension that must be measured. A typical application will require that the sensor determine the true position of a feature on a surface or a datum with a resolution of at least 500 µm in a 500 mm field of view. The typical requirement for porosity inspection on machine aluminum components used by the automotive industry is for the detection of an object 400 μm in diameter. The detection and measurement of a 400 μm imperfection will require a sensor with a resolution of at least 125 μm per pixel. The state of the art image sensor available at present provides a resolution of 16 mega-pixel or 4,000×4,000 pixels. The selection of the sensor is also influenced by the shape of the sensor's array. An 8 mega-pixel sensor has an array of 3500×2600 pixels. This shape is more conducive to long narrow components, such as found in the shape of many automotive components, i.e. engine heads and manifolds.

Figure 2:
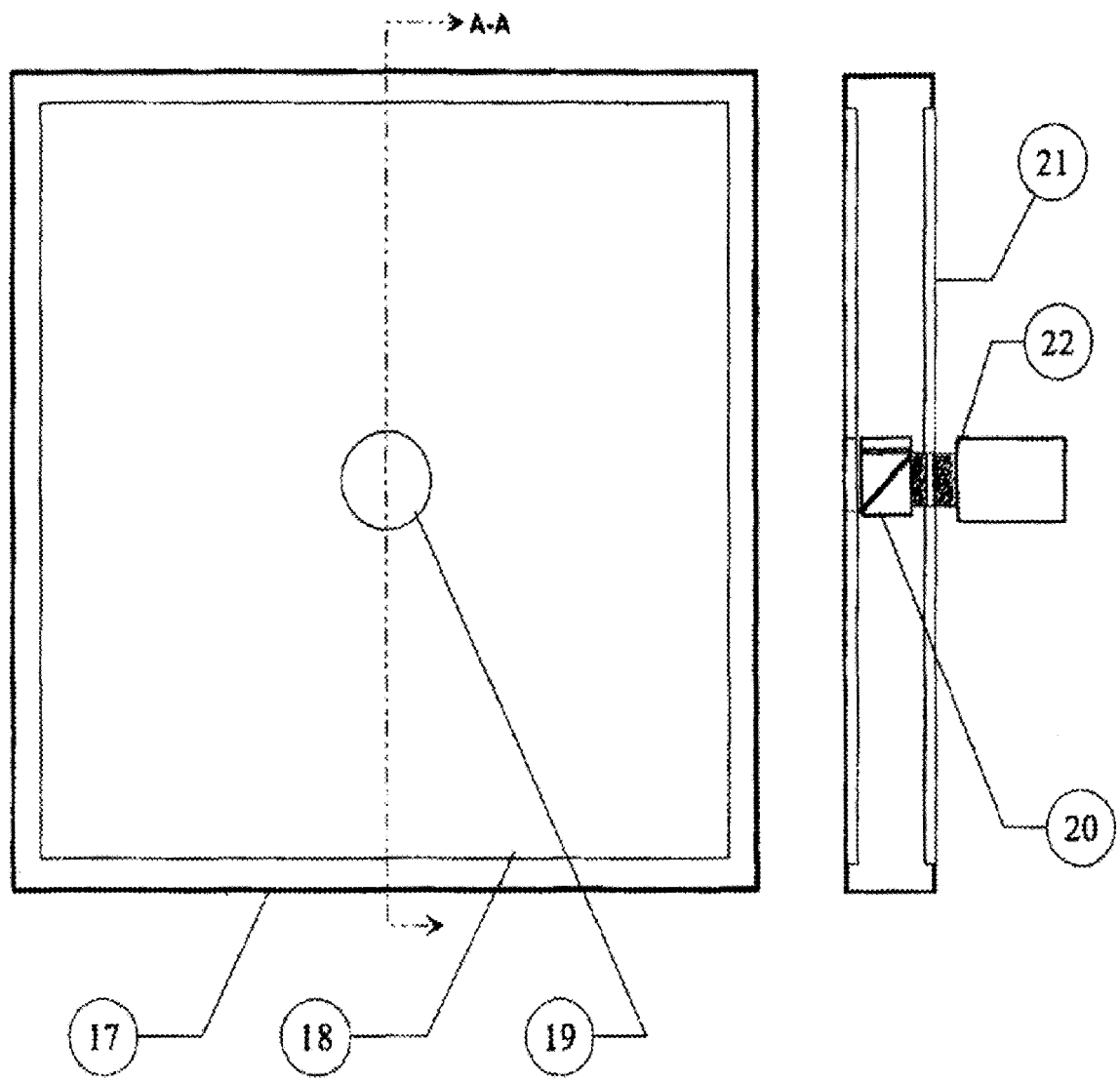

In special cases when the sample is relatively small, a diffuse front lighting source may be implemented. The illumination source illustrated in FIG. 2 can be used for the inspection of components that are smaller than 400 mm×400 mm in size and can be held normal to the inspection axis during image acquisition. The main housing (item 17) of the diffuse front lighting system is normally constructed of weld sheet metal or aluminum panels. The front diffusing panel (item 18) can be constructed of milk white polycarbonate sheet, acrylic sheet, or safety glass frosted on one side. The front diffusing panel is designed to fit securely in an access panel attached to the main housing. The exit window or aperture (item 19) is cut in the center of the front diffusing panel and is sized as small is possible without obstructing the optical path of the image sensor (item 22). In instances that the optical system does not require a beam splitter (item 20) to hide the aperture for the sensor, a glass cover is attached to prevent contamination from entering the main housing. The small profile of the main housing makes it an ideal candidate for the use of LED or Electro-illuminescent panel to provide the illumination. The use of an LED panel or Electro-illuminescent panel allows the manufacture of an extremely thin the illumination system. The LED panel configuration also has the benefit of low heat production because it can be strobed or turned on only when needed. The most common configuration of the diffuse front lighting system incorporates fluorescent lamps with high frequency drivers because of the lower cost.

The present invention provides a method by which the user may select specific regions of the image for analysis. Further, the present invention provides a method by which the user may apply specific inspection criteria to different regions or inspection zones in the image. FIG. 3 illustrates a component that is to be inspected using the present invention. The image is that of a cast aluminum automotive component that has machined features on surface being inspected (the sample). The sample is located in the inspection cell using dowel pins inserted into locating holes (items 25 & 26). The first operations in the machining sequence locate datum (items 23 & 24). All of the other features present on the sample are relative to the datum locations. The present invention accurately locates the location of the datum and will position all the inspection zones relative to the datum.

Figure 4:
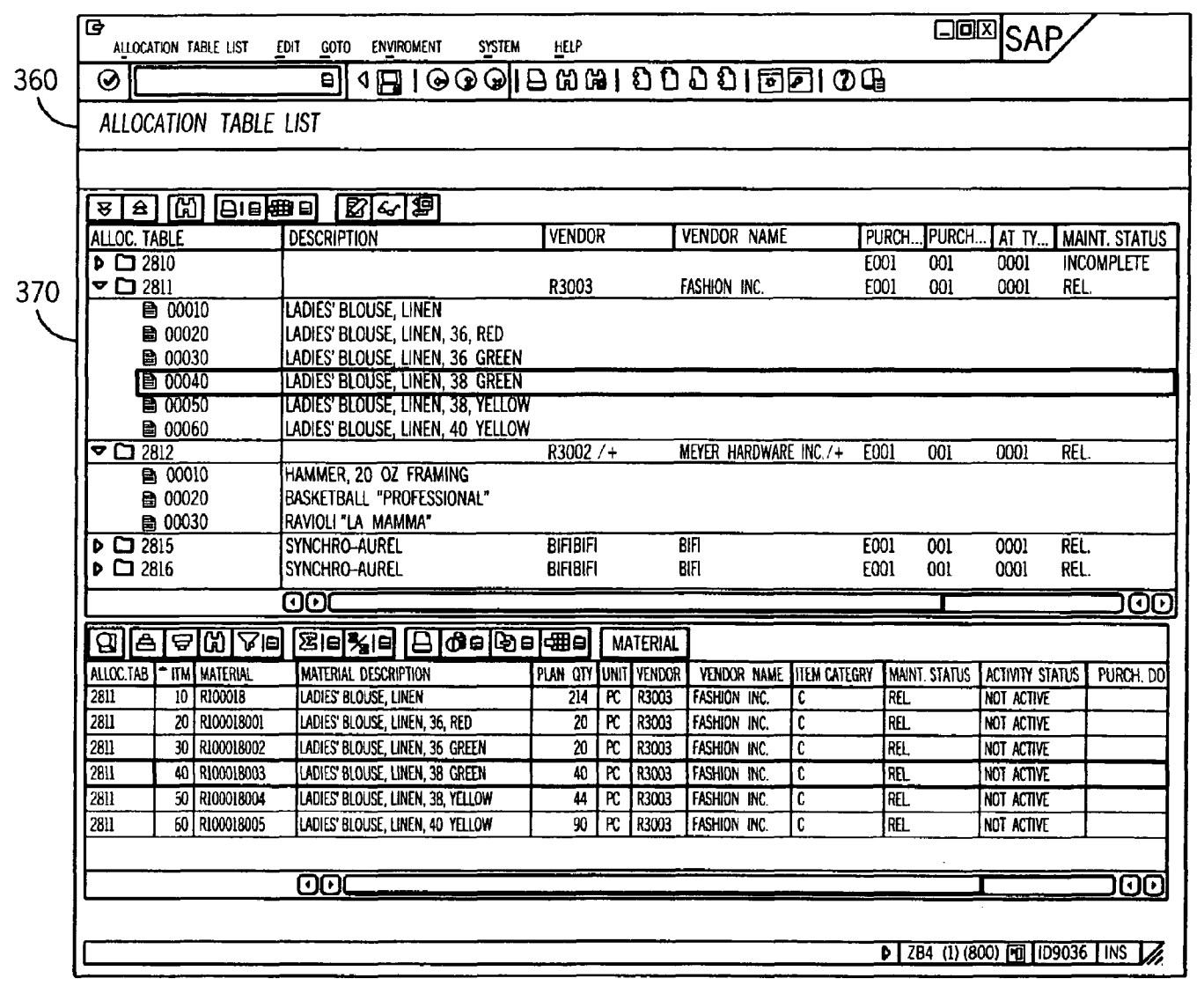
Figure 7:
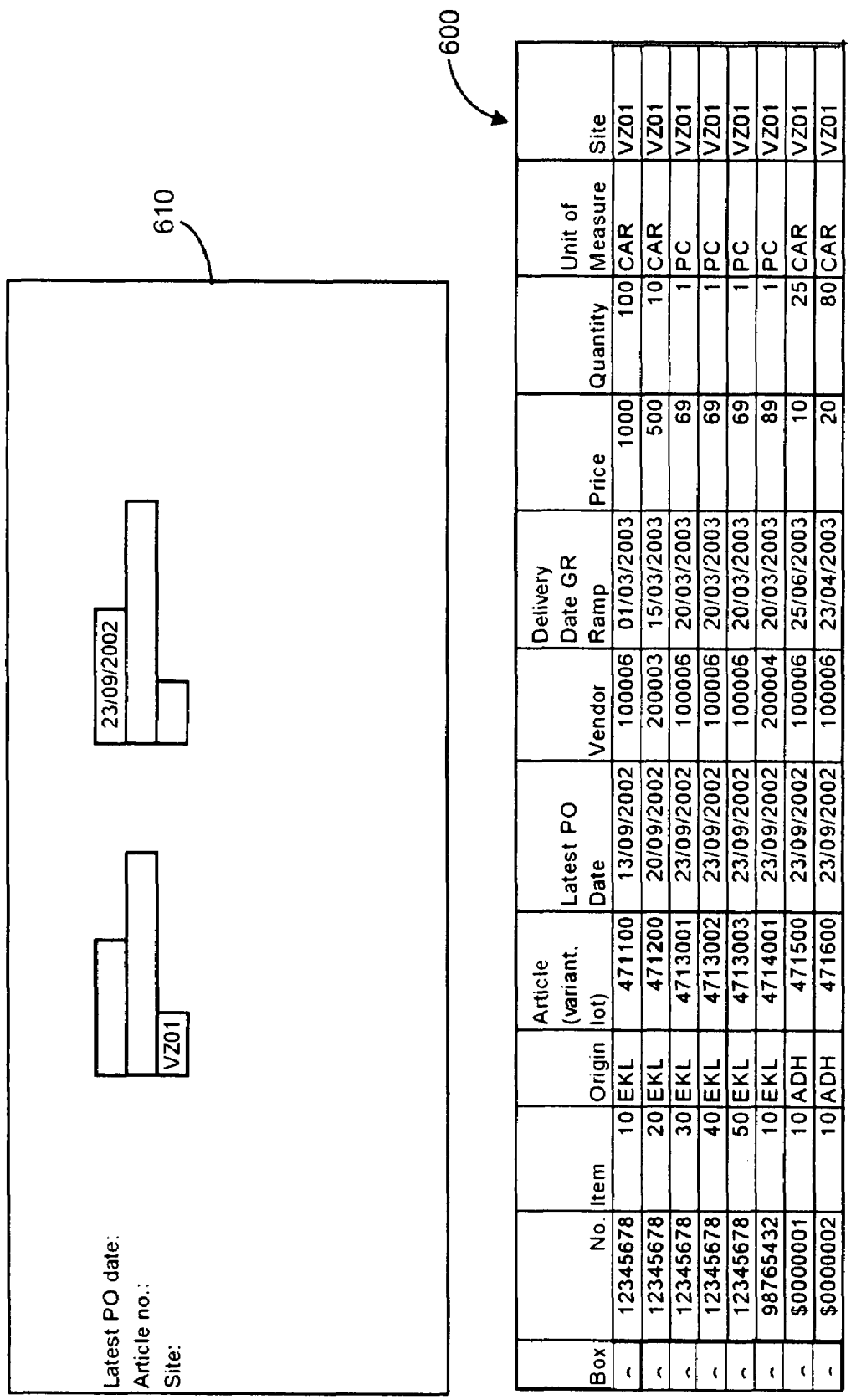
FIG. 7 illustrates the T-Slot Inspection Zone on image of test component.
Figure 8:
FIG. 8 illustrates the Tapped Hole Inspection Zones on image of test component.
Figure 1:
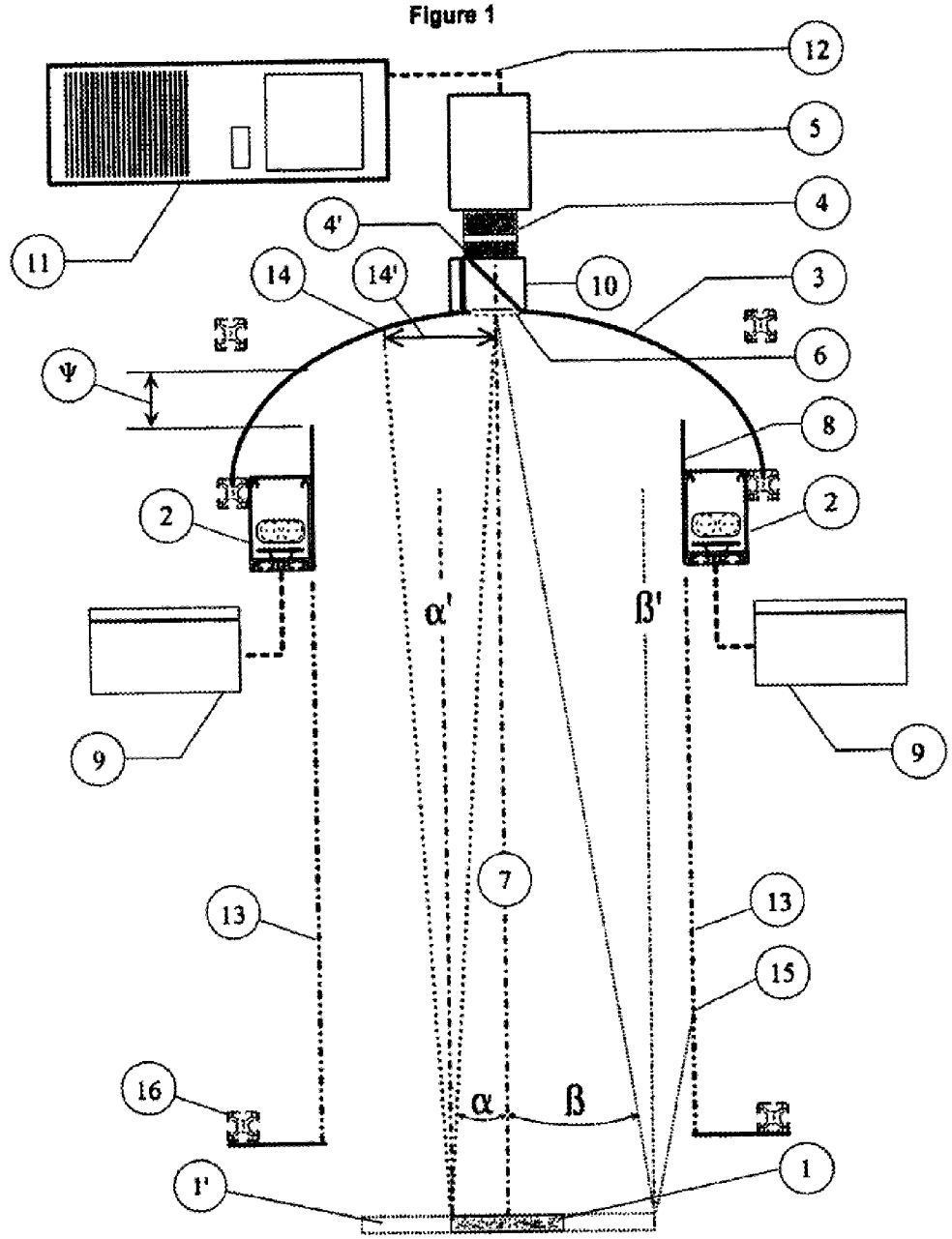

FIG. 4 illustrates the Outer Inspection Zone on the sample and its position is indicated by item 27. The Outer Inspection Zone is a sealing area and must be free of porosity and gouges. The criteria used for the inspection of this zone are pretty tight. FIG. 5 illustrates the Inner Inspection Zone (item 28) that is to be applied to the sample in an area where material was removed. The inspection criteria for this zone is more tolerant that for the Outer Inspection Zone because it is contained inside the engine. FIG. 6 illustrates the Worm Trail Inspection Zone that is to be applied to the sample. The Worm Trail (item 29) is actually a cast feature and is not machined. However, the position of the Worm Trail is critical and its location must be determined accurately to insure proper oil pressure in the final application. The Worm Trail Inspection mask must fit completely inside the worm trail of the sample or it must be rejected. FIG. 7 illustrates the T-Slot Inspection Zone (item 30) on the sample. There are four areas, not physically connected to each other that use the same inspection criteria. The position of T-Slots relative to each other and the datum are critical for proper operation. FIG. 8 illustrates the Hole Inspection Zone in which each of the drilled and tapped holes must be inspected for their location and the presence of threads. There are 20 features that must be located in this zone, one of them is identified as item 31.

The detailed method of training for the sample component illustrated in FIGS. 3 through 8 are listed below:

- (a) a "master" component, one that has been checked as meeting all the specifications necessary to qualify as a nominal part, is positioned in the image acquisition station of the invention;
- (b) the illumination system used must be at least three times larger than the component in all dimensions and must provide substantially uniform lighting across the entire surface to be inspected and implements a closed-loop feedback system to insure that the luminous flux output of the lamps are held at a constant level;
- (c) a image sensor is selected provides a minimum of 10 bits of grayscale resolution and provides a minimum spatial resolution so that the minimum size defect that must be isolated will be at least 3×3 pixels in size;
- (d) an image of the master component is acquired using the same equipment and conditions that will be used for analysis of production components;
- (e) the location of the datum on the master are extracted from the image accurately using special software;
- (f) a set of inspection mask are created using the features of the master component and stored relative to the location of the datum;
- (g) a set of inspection algorithms are developed to extract and measure the relevant features located in each of the masks (zones) that correspond to the inspection criteria of each zone;
- (h) all the inspection criteria relevant to the model (part number) are to be stored in the inspection system database.
- (i) if more than one surface of the component is to be inspected, steps a) through h) are repeated for each sensor/image processing combination used in the system;

The method used by the present invention for the inspection of production components comprises the following steps:

- (j) the model (part number) of the component to be inspected by the system is selected from the system database;
- (k) the test component is precisely located inside the inspection chamber, positioned with the aid of locating pins, physical stops or recessed lock positions within the inspection fixture;
- (l) the illumination system is constantly monitored and is in "Regulation" indicating that it is functioning as required and will provide substantially uniform lighting across the entire surface to be inspected;
- (m) the invention acquires the necessary image or images;
- (n) the location of component is determined precisely by the image processing software using the cast or machined datum of the surface to be inspected;
- (o) the image or images are translated (and rotated if necessary) to coincide with the datum of the reference images;

(p) each mask (inspection zone) and corresponding vision algorithm is applied to the acquired image and the result is then stored in the appropriate database register;

(q) the inspection criteria is applied to results of each corresponding inspection zone and evaluated to determine if the test component pass or failed;

(r) the sequence of steps p) and q) are repeated until all inspection zones have been evaluated, then an overall inspection result is posted in the cell controller for the component;

(s) each components test either was previously marked with a unique identification or will be marked at the conclusion of the inspection for traceability;

(t) components marked prior to entering the inspection station will have the identification read, using optical character recognition, 2-D code matrix, radio frequency tag or other means, to associate the inspection results to the component;

(u) components not marked prior to entering the inspection station will be marked with a unique code before being released and associated results recorded in the database;

(v) the invention has the ability to record the every image and the location of any defective conditions in the image in the database;

(w) the complete database and all associated images are stored on optical disk for future review;

(x) the steps k) through w) are repeated for each component to be inspected of the same model (part number), the sequence will begin with j) when a new model is selected;

(y) as an option the invention can send the inspection results via an Ethernet connection from any time period to a list of recipients at a specified time each day or day of the week;

(z) if the invention isolates "n" number of defective conditions occurring as run, trend or out of range a message is sent the a list of recipients immediately for action;

The present invention has the ability to identify the size and location of imperfections on individual components. A further benefit of the invention is that it can accumulate the inspection information over a number of samples over an extended period. This allows the invention to product a concentration map of specific defect types. The concentration map will provide the number and locations of defects graphically on the operator interface of the Cell Controller. FIG. 9 represents the location of imperfections in several Inspection Zones for a 16-hour period. The high concentration of porosity defects in the Outer Inspection Zone (item 32) indicates that there is a solidification problem in that region. The imperfection isolated on opposite side of the part (item 33) indicates that this is most likely a random occurrence and is less critical. The various types of imperfections are display as different color markers on the operator interface screen of the present invention.

Figure 10:
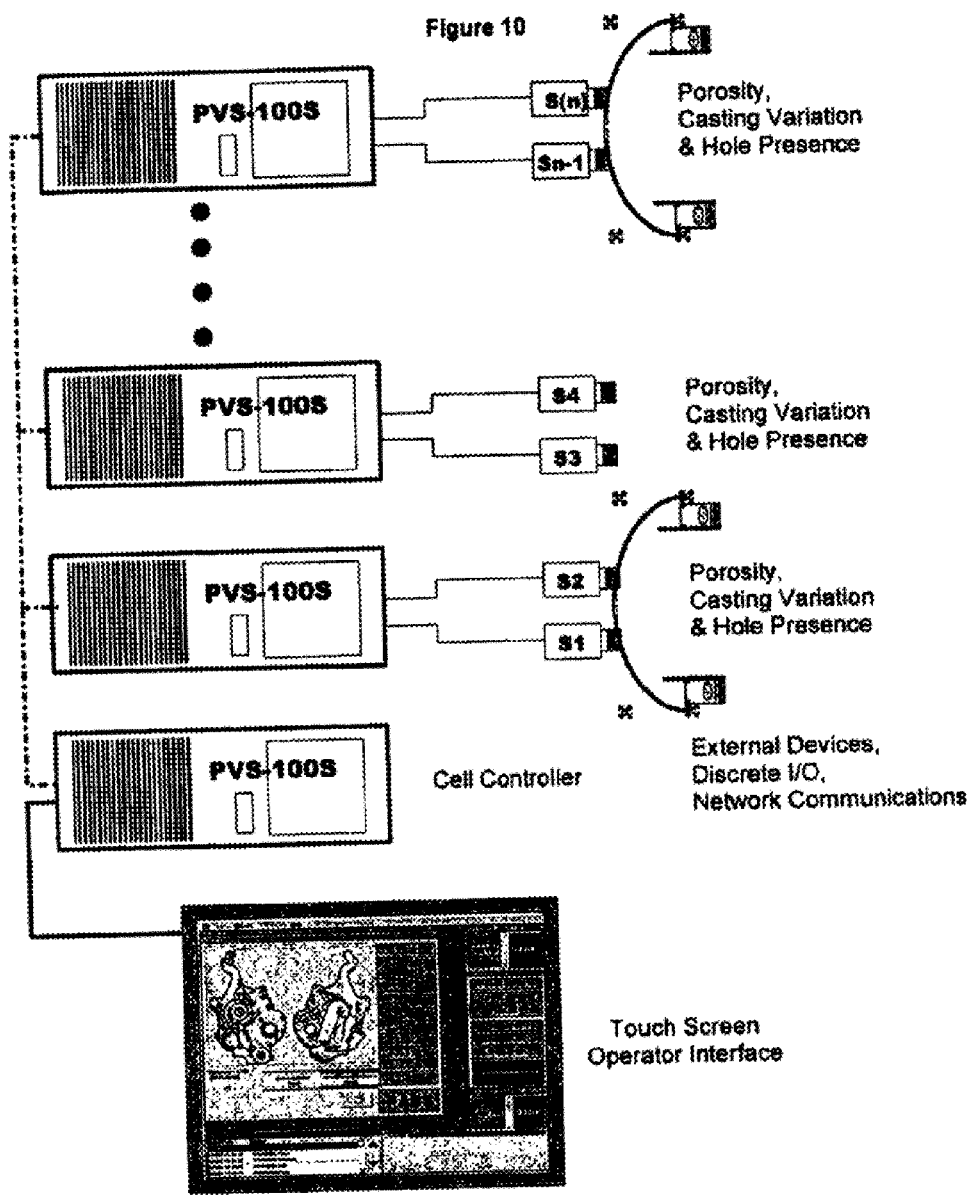
FIG. 10 illustrates typical configuration of a multiple image processor cluster for the division of image processing task with Touch Screen Operator Interface connected to the Cell Controller.
Figure 1:
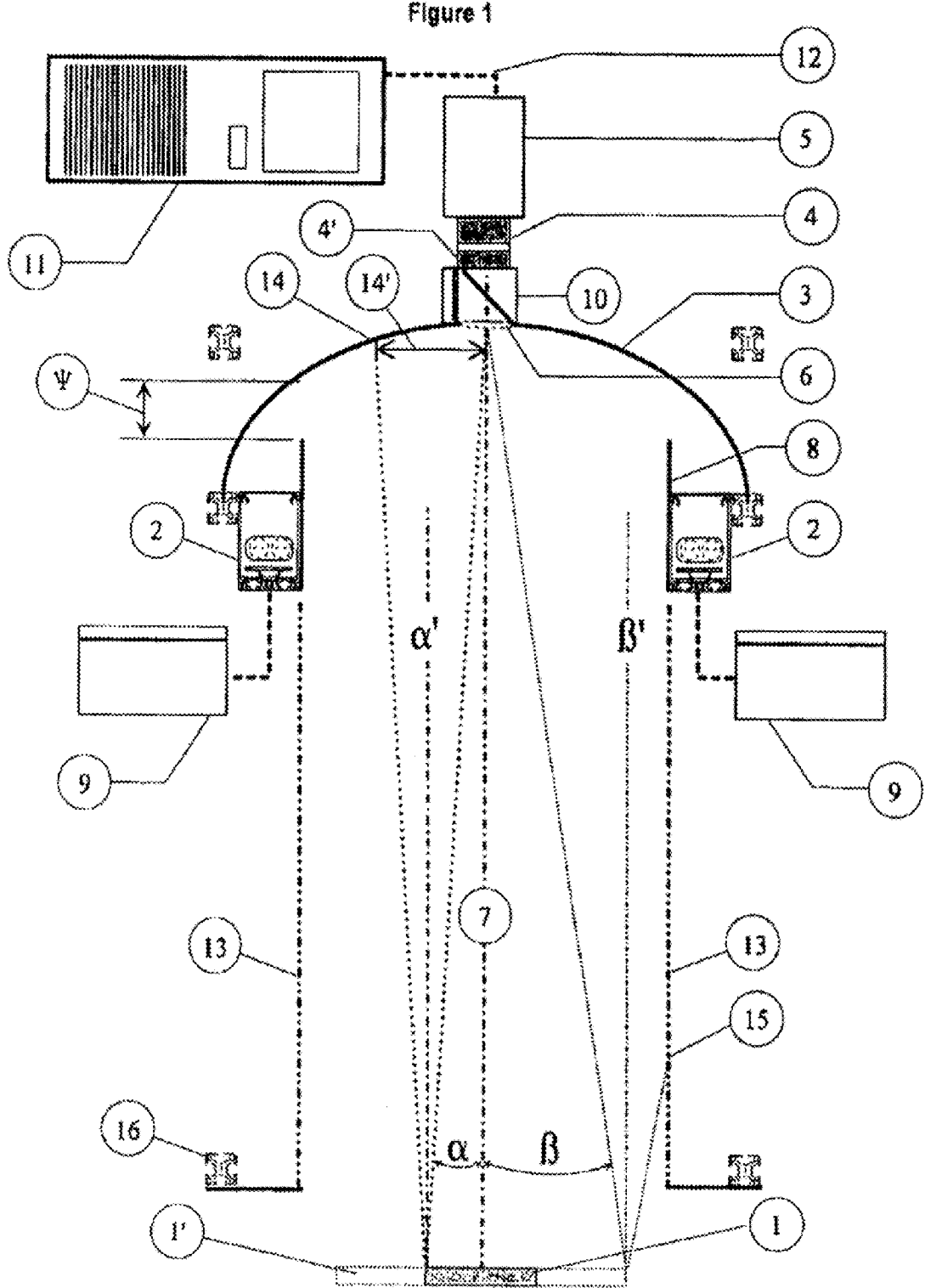

In applications, with requirements for multiple sensors it may be necessary to implement additional image processors. FIG. 10 illustrates a multiplicity of inspection stations controlled by Cell Controller. The present invention implements special proprietary software that controls the operation of system. This software is protected by copyright law and is considered a trade secret by the inventor. For purposes of the present invention, the software is considered an integral component of the image processing equipment. The software is designed to collect the results of multiple inspection operations and place them in a database. The inspection operations may occur in a single image processing unit or distributed over several image-processing units that make up the entire inspection cell. The inspection cell that incorporates three or more image processing units may require that a separate computer system be implements as a dedicated "Cell Controller". The purpose of the Cell Controller is direct the operation of the individual image processors, coordinate the transfer of information to/from devices, compile inspection data and images, and determine the final status of a sample in the inspection cell.

In the case of large sample it is often more convenient to perform the inspection of the separate surface in separate inspection chambers. Large components, such as automotive engine components, inspected in sequential inspection chambers. The size of the inspection chamber is typically four times the size of the component being inspected, for example a 400 mm×150 mm components will require an inspection chamber that is 800 mm×300 mm. The entire inspection system might incorporate three or more inspection chamber of this size arranged in side by side configuration. The most common sample transfer systems utilize lift and carry, powered pallet, pallet on powered roller conveyor or indexing dial tables. The inspection system will be configured to adapt to the transfer method and position the inspection axis normal to the sample surface being inspected.

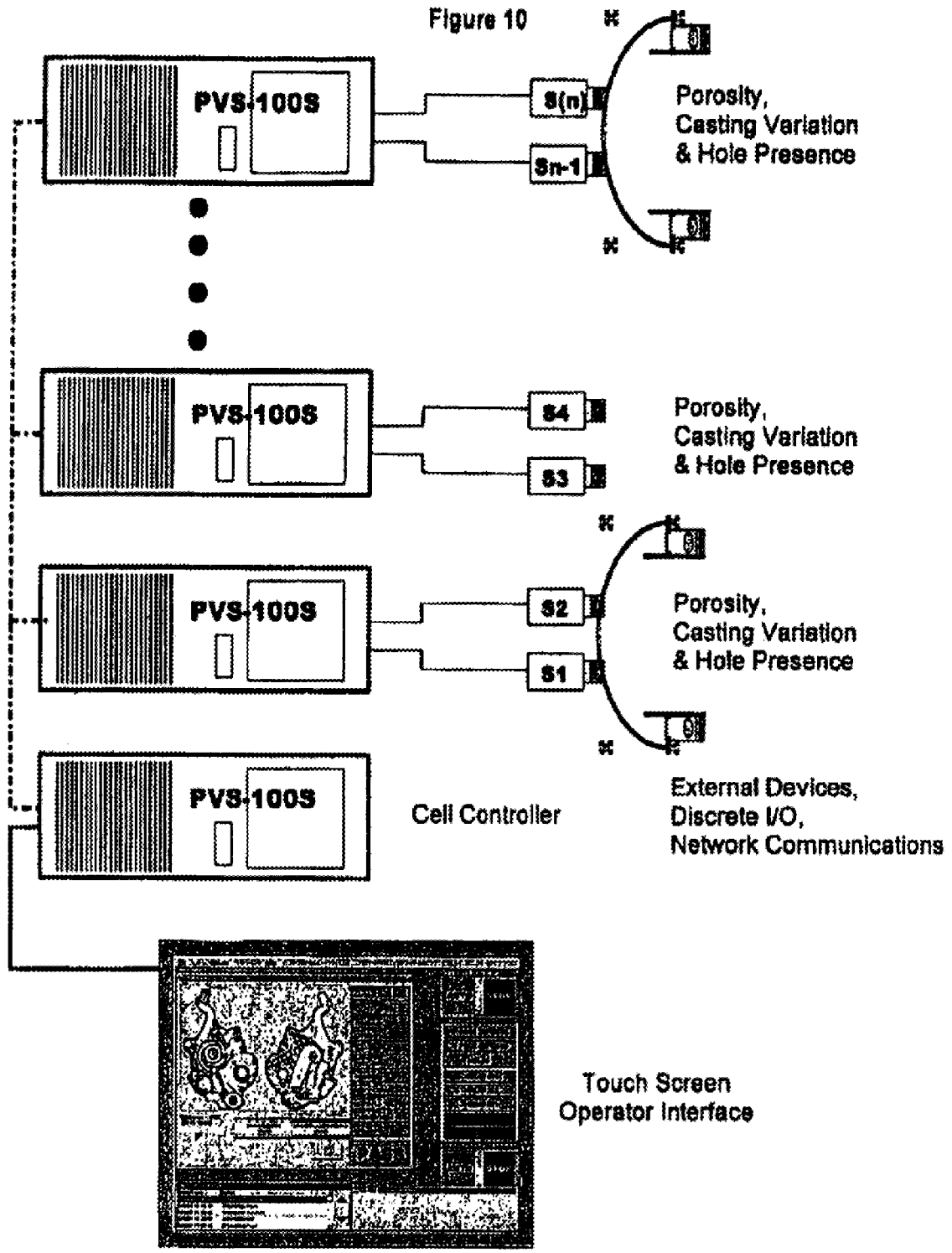

The invention claimed is:

1. A apparatus with large diffuse illumination area which permits the measurement and determination of key characteristics of large machined metal components used in internal combustion engine manufacturing with a machine vision measuring system comprising:

a) an image processing computer for image acquisition, image storage and image processing capability;

b) the image processing computer comprising memory for storing the images formed by the camera;

c) the image processing computer also comprising digital parallel input/output digital serial, and Ethernet communication capabilities for providing messages to external devices to report one or more measurements or characteristics of the machined metal surface;

d) the image processing computer executing control software stored in a computer-readable medium, which allows request and response signals from external devices indicating a machine machined metal component to be inspected, which causes the image processing computer to perform image alignment and analysis for extraction of key characteristics of the machined metal component, as well as causing the image processing computer to store a reference images of an acceptable quality machined component in a memory location referenced by a specific identification code that is unique to a specific machined component model or type, as well as causing a determination of the exact position of the machined component by extracting one or more edges or edge points of the machined datum based on grayscale sub-pixel information;

e) one or more image sensors with appropriate lens for providing a spatial resolution and depth of field necessary to form a sharp focus image of the surface of the machined metal component or a target portion thereof including the machined datum;

f) wherein each image sensor comprises sufficient pixel resolution to resolve an imperfection on the surface of the machined metal component;

g) an illumination system comprising: a large tunnel structure with diffuse interior surface with a projected area in the inspection plane approximately three time the area of the machined metal component;

h) wherein the illumination system is positioned above the machined metal component so that the major axis of the large tunnel structure with diffuse interior surface is oriented parallel to the major axis of the machined metal component;

i) wherein the illumination system has fluorescent lamps positioned so that the lamps illuminate the large tunnel structure with diffuse interior while preventing direct illumination from the lamps on the machined metal component or the optics of the image sensor;

j) wherein the illumination system implements precision power supplies with controlled feedback circuit with a photo-electric sensors to measure the luminous flux of the fluorescent lamps, providing adjustment in filament current to maintain a pre-selected output level;

k) wherein the illumination system uniformly illuminates the entire surface to be inspected;

l) one or more image sensors are positioned relative to the machined metal component, a wherein the focal point of detection coincides with the surface of the machined metal component so to view a feature to be measured with sharp focus;

m) wherein the illumination system provides a contrasting geometric size and shape of all of the features on the machine metal surface being inspected.

2. An apparatus as recited in claim 1, wherein the executed control software provides for: acquiring of a test image of new or previously taught machined metal component and storage of the test image in memory and determining the exact position of a machined metal component in the test image by extracting one or more edges based on grayscale image or grayscale sub-pixel information extracted from the grayscale image; alignment of a stored reference image of a master reference component and the test image of the machined metal component by translation of the test image to coincide with datum points of a reference image; determining if a difference exists between the stored reference image of the master reference and the test image of the machined metal component by means of a grayscale image subtraction and storing the result in a difference image; determining if the machined metal component being tested is out of position as determined by a shift in reference point information; and generation of an error message to an external device indicating the isolation of a defective setup condition on the machined metal component tested.

3. An apparatus as recited in claim 1, wherein the executed control software provides for: acquiring of a test image of a machined metal component and storage of the test image in memory; determining the exact position of a machined metal component in the test image by extracting one or more edges based or grayscale sub-pixel information; determining if a difference exists between the stored reference image of the master machined metal component and the test image of the test machined metal component by means of a grayscale image subtraction and storing the result in a difference image in memory.

4. An apparatus as recited in claim 1, wherein the executed control software provides for: acquiring of a test image of a machined metal component and storage of the test image in memory; determining the exact position of the machined metal component in the test image by extracting one or more edges based on grayscale sub-pix& information; determining if a difference exists between the stored reference image of a master machined metal component and the test image of the machined metal component by means of a grayscale image subtraction and storing the result in a difference image; determining if the machined metal component is defective by an absence of material in regions or inspection zones where material should be present as determined by a lack of grayscale information around feature profile, and generation of an error message to a external device indicating the isolation of a defective condition on the machined metal component.

5. An apparatus as recited in claim 1; wherein the executed control software provides for: acquiring of a test image of a machined metal component and storage of the test image in memory; determining the exact position of a machined metal component in the test image by extracting one or more edges based on grayscale image or grayscale sub-pixel information extracted from the grayscale image; alignment of a stored reference image of a mastered machined metal component and the test image of the machined metal component by translation of the test image to coincide with the edge points of the reference image; determining if a difference exists between the stored reference image of the machined metal component and the test image of the machined metal component by means of a grayscale image subtraction and storing the result in a difference image; determining if the machined metal component is defective by the presence of extra material or a change in the mold core position as determined by residual grayscale information in the difference image larger than a maximum number of pixels inside regions that no pixels should exist; and generation of an error message to a external device indicating a defective condition has been isolated on the machined metal component.

6. A method for measurement and determination of key characteristics of machined metal components used in heavy duty truck, off-road and automotive engines for line inspection, the method utilizing a machine vision measuring system and a computer comprising memory for executing control software embodied on a computer readable medium, to provide the steps of:

a) using a computer aided design (CAD) data file for extraction of key inspection features of machined metal component and relative position of key features to secondary datum in a memory location referenced by a specific identification code that is unique to a machined metal component model or type;

b) storing one or more reference inspection mask images of a new master machined metal component generated from CAD data or a master machined metal component in a memory location referenced by a specific identification code that is unique to a machined metal component model or type;

c) determining a position of the machined metal component in the reference image by extracting one or more edges, datum shapes or edge points based on a grayscale image or sub-pixel information in the grayscale image and storing the corresponding pixel locations;

d) determining a portion of the reference image that contains reference foreground grayscale image information that represents the surface of machined metal component;

e) determining the portion of the reference image that contains reference background information that excludes the machined metal component;

f) acquiring of a test image of a used machined metal component and storage of the test image in memory;

g) determining the position of the machined metal component in the test image by extracting one or more edges, datum shapes or edge points based on the grayscale image or sub-pixel information in the grayscale image and storing the corresponding pixel locations in memory;

h) determining the portion of the test image that contains the test foreground grayscale image information that represents the machined metal component;
i) determining the portion of the test image that contains the test background grayscale image information that excludes the machined metal component;
j) creating a background difference image by grayscale subtraction of the test background image from the reference background image;
k) creating a foreground difference image by grayscale subtraction of the test foreground image from the reference foreground image;
l) creating and storing in memory a background list of values comprising background grayscale objects representing resulting information in the background difference image larger than a pre-determined criteria;
m) creating and storing a foreground list of values comprising foreground grayscale objects representing resulting information in the foreground difference image larger than a pre-determined criteria;
n) reducing of the stored background list by applying pre-determined size and shape filtering algorithms;
o) reducing of the stored foreground list by applying pre-determined size and shape filtering algorithms for the removal of information associated with normal machining operations;
p) displaying an error message prompting a user that the machined metal component is defective and requesting removal of the machined metal component when more than a pre-determined number of values remain on the stored background and foreground lists after filtering;
q) displaying the inspection information from each test on a human machine interface and stored permanently on one of the internal storage hard drives or written to a recordable digital video disk for offsite record storage.

7. A method as recited in claim 6, further comprising the steps of: determining the size of a grayscale object in the foreground difference image in pixels; determining the size of the grayscale object or objects are larger than a pre-determined criteria; and generating an error message that prompts the user that the machined metal component is defective and requests removal from manufacturing line.

8. A method as recited in claim 6, further comprising the steps of: determining the size of a foreground grayscale object in the foreground difference image in pixels; adding the foreground grayscale object in the foreground difference image with the appropriate inspection mask and storing the temporary inspection result; determining the size of the foreground grayscale object in the temporary inspection result is smaller than a first pre-determined criteria and larger than a second pre-determined criteria, as can be associated with the surface texture of milling operations; generating an message that prompts a user that the machined metal component is acceptable; repeating for each of the inspection mask stored.

9. A method as recited in claim 6, further comprising the steps of:
the archival storage of inspection results including, number, size, aspect ratio, position, inspection zone, sample number, relevant images, time, date and other inspection specific information in a database.

10. A method as recited in claim 6, wherein the inspection technique is able to accommodate the inspection of large components, up to 1,000 mm×650 mm, using the appropriate illumination and optical systems.

11. A method as recited in claim 6, further comprising the steps of: an inspection window larger than the component being inspected allowing the machined metal component that is to be tested to float as long as it stays inside the field of view of the sensor, thus the invention locates the machined metal component for automatic alignment even if the component is not in a locked in a fixture or predetermined inspection position on a conveyor.

12. A method as recited in claim 6, wherein the inspection technique using the appropriate sized image sensor is capable of resolving features and extracting the distance between datum so as to perform measurements equivalent to ±0.2 pixel.

13. A method as recited in claim 6, wherein the one or more inspection zones are applied to the inspection of each sample using a single image and a different inspection algorithm and a different inspection specification is applied to each inspection zone.

14. A method as recited in claim 6, wherein the measurement and position determination of surface imperfections, namely porosity defects, calculates the relative proximity of one defect to another over the surface of the entire component using a single image to determine if a sample is above or below the inspection specification.

15. The method of claim 6, wherein the measurement and position determination of surface imperfections is performed more accurately using a single image of the entire component, due primarily to the lack of multiple sensor alignment errors, multiple sensor sensitivity variations and the image overlap between sensors.

16. The method of claim 6, wherein the described system is capable of detecting and measuring casting variations in which a mold core has shifted, a mold has broken or a part of the mold was out of place before the metal pouring operation.

17. The method of claim 6, wherein the measurement of surface features is capable of detecting missing machining operations, often referred to as non-clean up of the surface.

18. The method of claim 6, wherein point cloud measurements for the defects over a period can be generated to assist the foundry by identification of areas where defect (porosity) levels have a high level of incidence and are exposed after machining operations.

19. The method of claim 6, wherein the system provides an identification of individual component faults and provides a visual indication of the defect location on the operator interface monitor.

20. The method of claim 6, wherein the system allows traceability of individual acceptable components inspection results and visual records directly from the inspection system to manufacturing personnel, product engineers, administrative personnel and the ultimate customer at a predetermined time using the internet, thus optimizing scheduling and reducing the number of false non-conforming product claims.

* * * * *

UNITED STATES PATENT AND TRADEMARK OFFICE
CERTIFICATE OF CORRECTION

PATENT NO. : 7,394,530 B2
APPLICATION NO. : 11/095960
DATED : July 1, 2008
INVENTOR(S) : Gerald Budd It is certified that error appears in the above-identified patent and that said Letters Patent is hereby corrected as shown below:

In the drawings, delete figures 3 thru 11 and insert the following figures 2 thru 10:

Signed and Sealed this

Fourteenth Day of October, 2008

JON W. DUDAS
*Director of the United States Patent and Trademark Office*

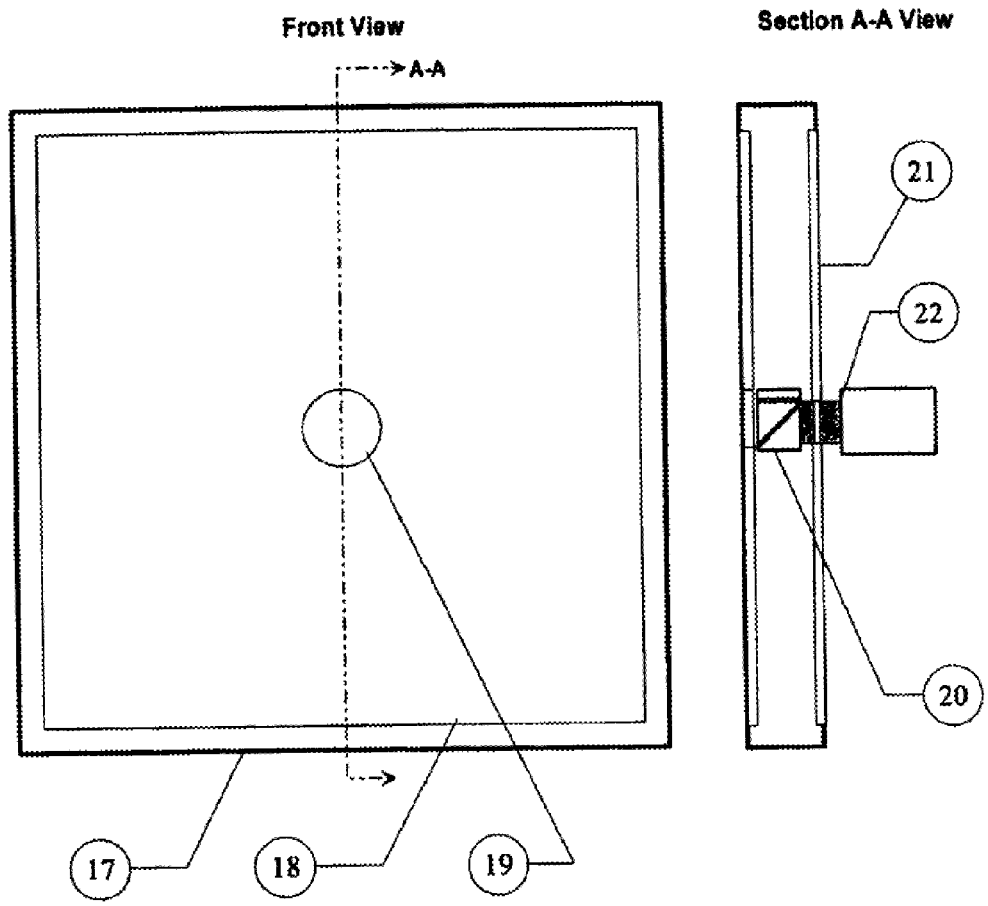

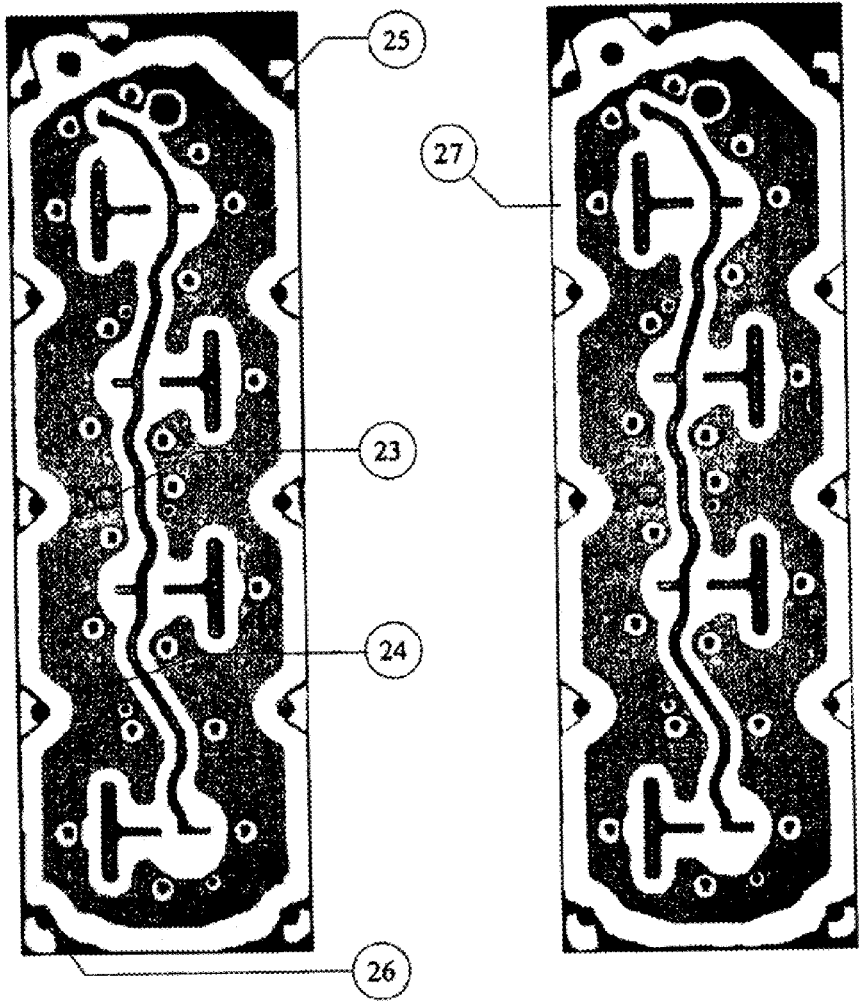
Figure 3 - The Original Part
Figure 4 - Outer Inspection Zone

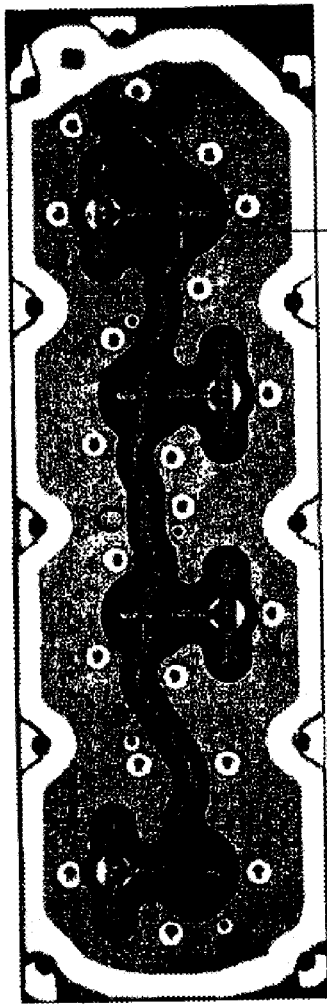
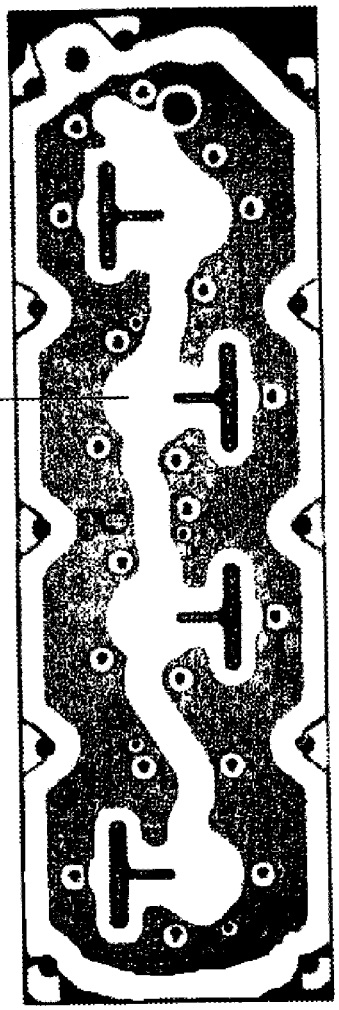
Figure 5 - Inner Inspection Zone
Figure 6 - Worm Trail Inspection Zone

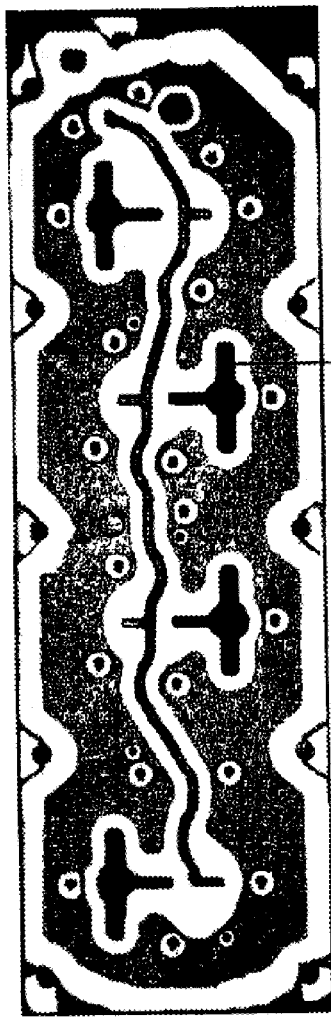
Figure 7 - T-Slot Inspection Zone
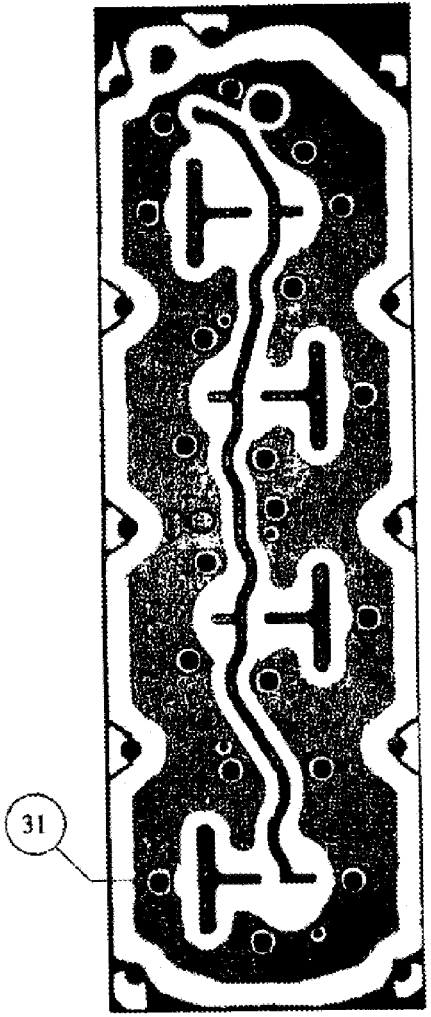
Figure 8 - Hole Inspection Zone

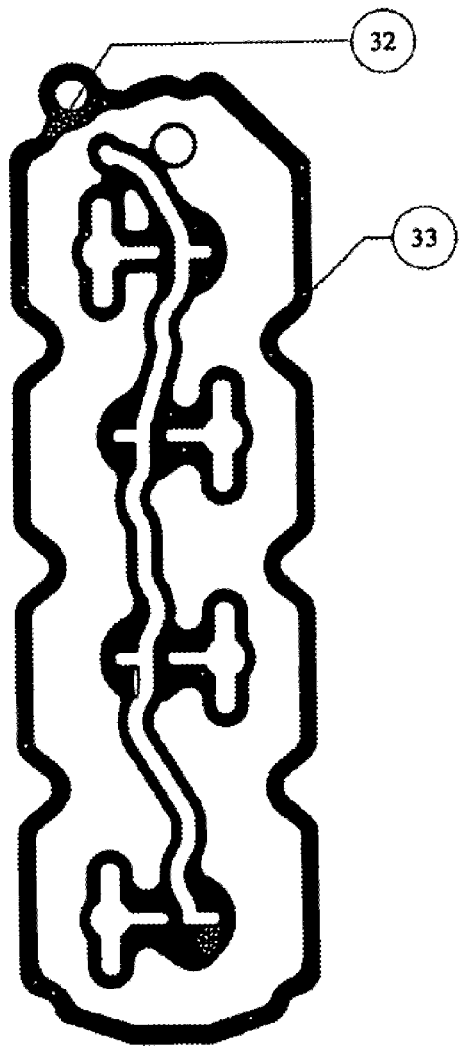
Figure 9 - Defect Mapping

UNITED STATES PATENT AND TRADEMARK OFFICE
CERTIFICATE OF CORRECTION

| | | |
|---|---|---|
| PATENT NO. | : 7,394,530 B2 | |
| APPLICATION NO. | : 11/095960 | |
| DATED | : July 1, 2008 | |
| INVENTOR(S) | : Gerald Budd | |

It is certified that error appears in the above-identified patent and that said Letters Patent is hereby corrected as shown below:

Delete the title page and substitute therefor the attached title page.

Delete Drawing Sheets 1-10, consisting of FIGS. 1-11, and substitute therefor the attached Drawing Sheets 1-7, consisting of FIGS. 1-10.

This certificate supersedes the Certificate of Correction issued October 14, 2008.

Signed and Sealed this

Fourth Day of November, 2008

JON W. DUDAS
*Director of the United States Patent and Trademark Office*

(12) United States Patent
Budd

(10) Patent No.: US 7,394,530 B2
(45) Date of Patent: Jul. 1, 2008

(54) SURFACE INSPECTION TECHNOLOGY FOR THE DETECTION OF POROSITY AND SURFACE IMPERFECTIONS ON MACHINED METAL SURFACES

(76) Inventor: Gerald W. Budd, 36853 Heafferon Rd., Farmington, MI (US) 48335

(*) Notice: Subject to any disclaimer, the term of this patent is extended or adjusted under 35 U.S.C. 154(b) by 334 days.

(21) Appl. No.: 11/095,960

(22) Filed: Mar. 30, 2005

(65) Prior Publication Data
US 2005/0220335 A1 Oct. 6, 2005

Related U.S. Application Data

(60) Provisional application No. 60/557,490, filed on Mar. 30, 2004.

(51) Int. Cl.
G01N 21/00 (2006.01)

(52) U.S. Cl. .................. 356/237.1; 356/237.2

(58) Field of Classification Search ............ 356/237.2; 148/420, 437, 237.2, 120; 164/46, 97, 113–114, 164/120–122, 487, 45, 420–437; 324/303; 429/13, 30, 40–44
See application file for complete search history.

(56) References Cited

U.S. PATENT DOCUMENTS

| | | | |
|---|---|---|---|
| 3,766,387 A * | 10/1973 | Heffan et al. | 378/58 |
| 4,583,993 A * | 4/1986 | Bhattacharya et al. | 250/359.1 |
| 4,803,639 A * | 2/1989 | Steele et al. | 702/40 |
| 4,819,256 A * | 4/1989 | Annis et al. | 378/87 |
| 5,715,334 A | 2/1998 | Peters | 382/254 |
| 6,693,708 B1 * | 2/2004 | Hunter | 356/237.5 |
| 6,718,053 B1 * | 4/2004 | Ellis et al. | 382/128 |
| 7,148,960 B2 * | 12/2006 | Schuster et al. | 356/237.6 |

* cited by examiner

*Primary Examiner*—Layla G. Lauchman
*Assistant Examiner*—Jarreas Underwood

(57) ABSTRACT

The present invention describes a method and apparatus for the detection and measurement of surface imperfections within a predetermined size range, contained on the surface of a machined cast metal component. The invention provides a novel illumination and image acquisition technique that allows the inspection of large cast machined surfaces without movement of the component, sensor or illumination system during acquisition of an image. The invention allows for the inspection of large surfaces on objects up to 1,000 mm×650 mm in size. The inspection field of view can be divided in multiple regions, defined by computer aided design (CAD) model data. Each of these regions may apply a unique set of inspection criteria used for disposition of the component. Inspection regions generated using CAD drawings indicate exact position of features with respect to the manufacturing datum located on the surface and viewable as part of the acquired image.

20 Claims, 7 Drawing Sheets

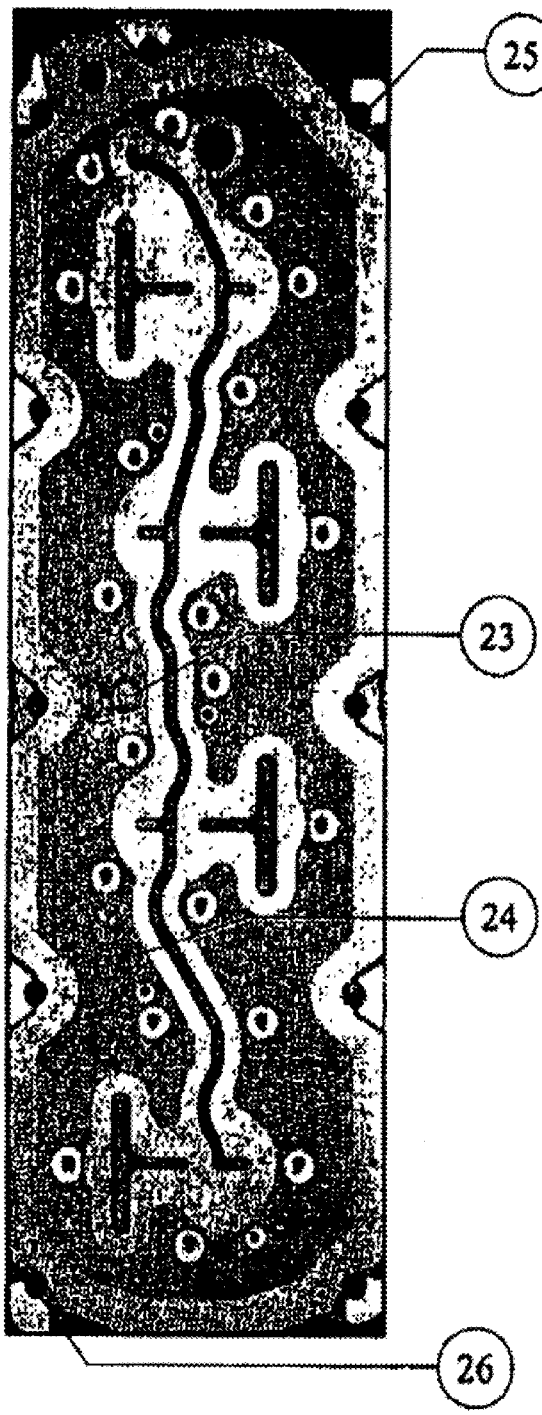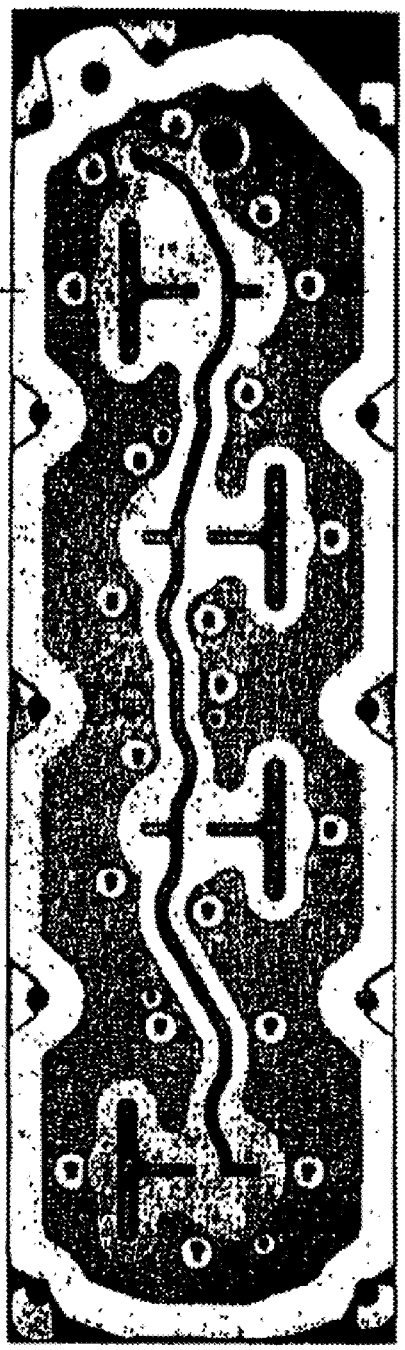
Figure 3 - The Original Part
Figure 4 - Outer Inspection Zone

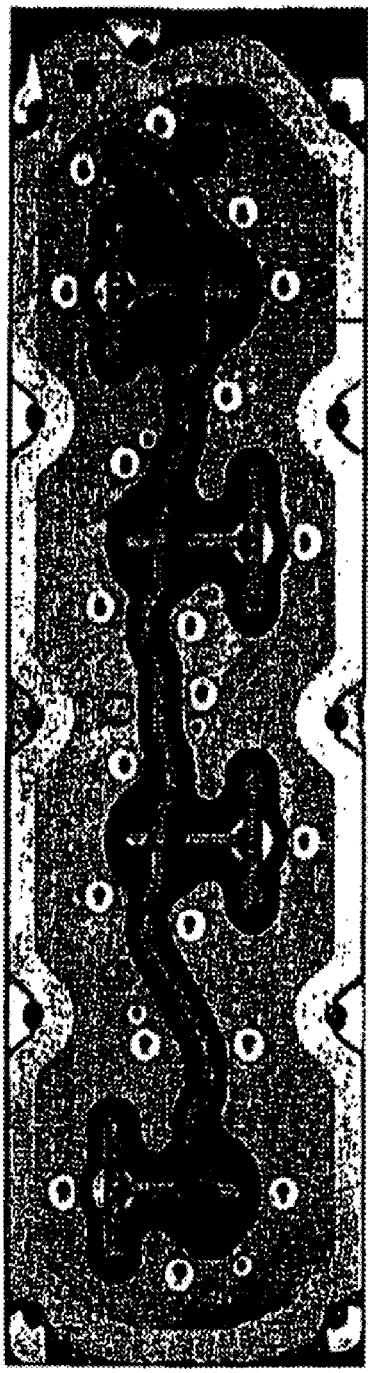
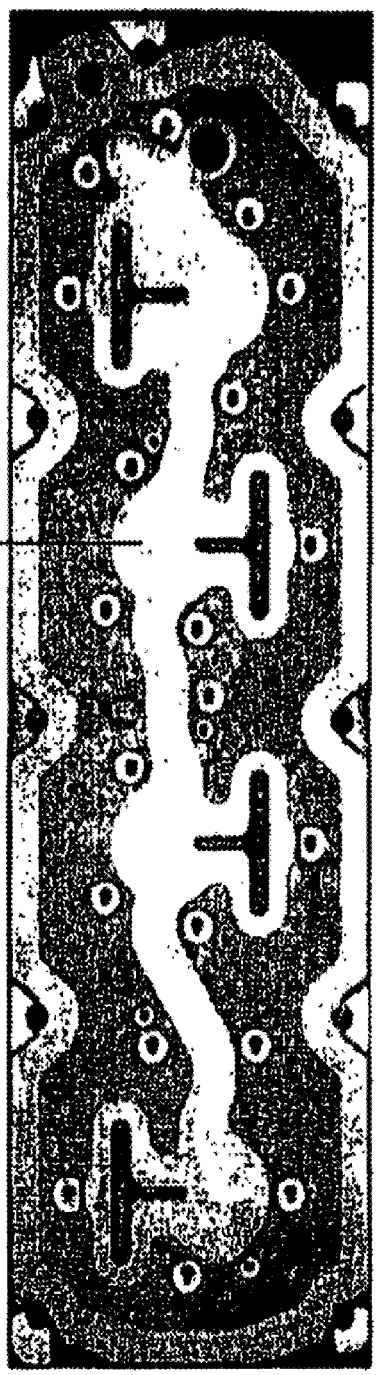
Figure 5 - Inner Inspection Zone        Figure 6 - Worm Trail Inspection Zone

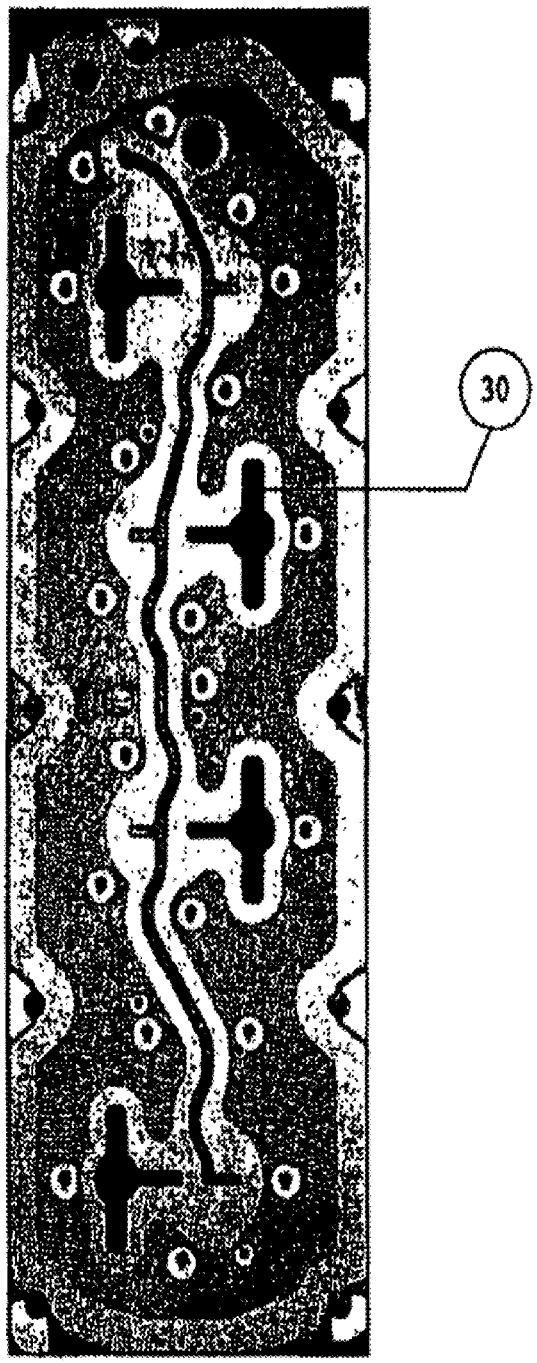 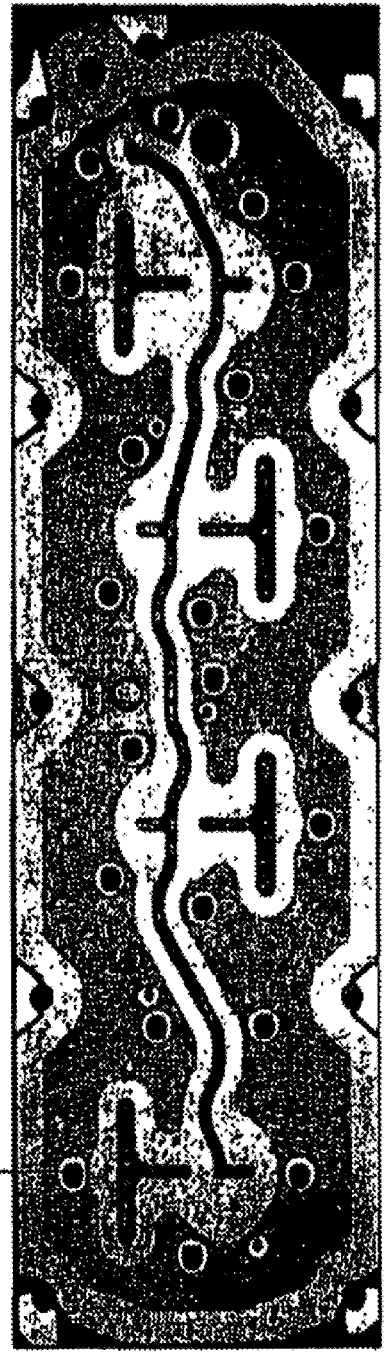
Figure 7 - T-Slot Inspection Zone     Figure 8 - Hole Inspection Zone

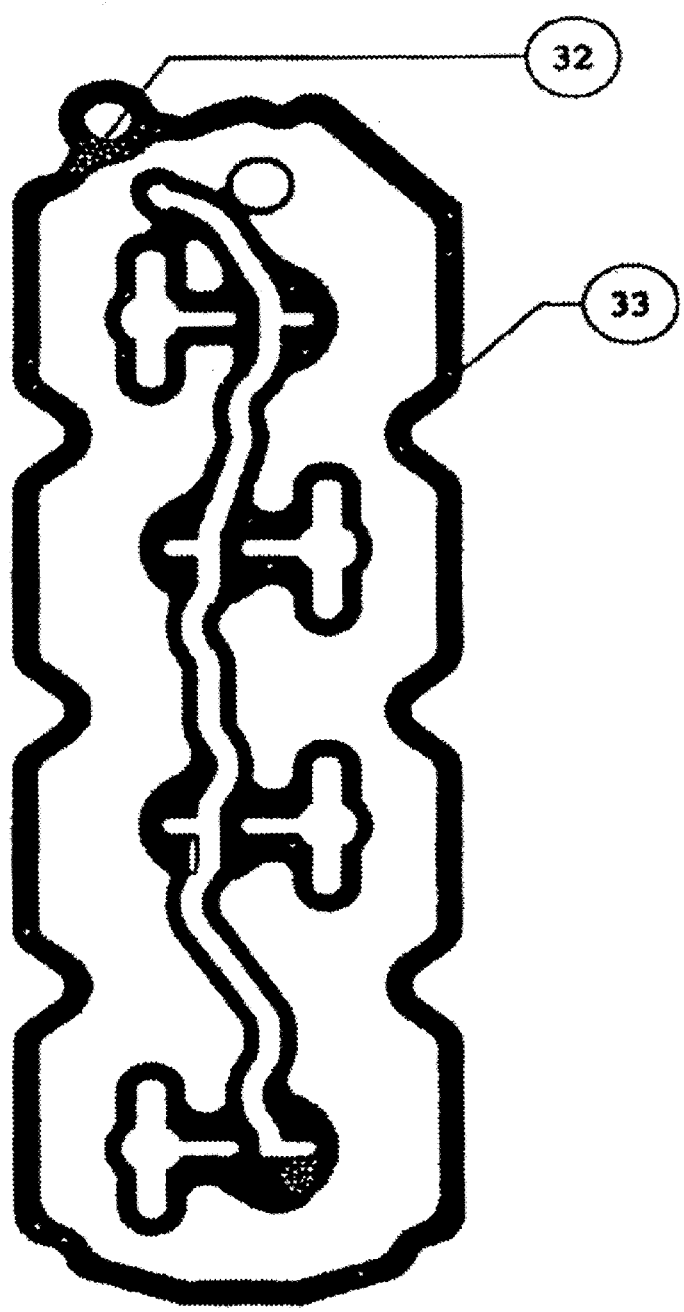
Figure 9 - Defect Mapping